US008758245B2

(12) United States Patent
Ray et al.

(10) Patent No.: US 8,758,245 B2
(45) Date of Patent: Jun. 24, 2014

(54) SYSTEMS AND METHODS FOR PATTERN RECOGNITION IN DIABETES MANAGEMENT

(75) Inventors: Pinaki Ray, Fremont, CA (US); Greg Matian, Foster City, CA (US); Aparna Srinivasan, San Jose, CA (US); David Rodbard, Potomac, MD (US); David Price, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 1726 days.

(21) Appl. No.: 11/688,639

(22) Filed: Mar. 20, 2007

(65) Prior Publication Data

US 2008/0234992 A1    Sep. 25, 2008

(51) Int. Cl.
*A61B 5/00*    (2006.01)

(52) U.S. Cl.
USPC .......................................... 600/365; 600/347

(58) Field of Classification Search
USPC ........................................ 600/345, 347, 365
See application file for complete search history.

(56) References Cited

U.S. PATENT DOCUMENTS

| 4,695,954 | A | 9/1987 | Rose et al. |
| 4,731,726 | A | 3/1988 | Allen, III |
| 4,779,199 | A | 10/1988 | Yoneda et al. |
| 4,817,044 | A | 3/1989 | Ogren |
| 5,019,974 | A | 5/1991 | Beckers |
| 5,216,597 | A | 6/1993 | Beckers |
| 5,251,126 | A | 10/1993 | Kahn et al. |
| 5,307,263 | A | 4/1994 | Brown |
| 5,319,363 | A | 6/1994 | Welch et al. |
| 5,341,291 | A | 8/1994 | Roizen et al. |
| 5,376,070 | A | 12/1994 | Purvis et al. |

(Continued)

FOREIGN PATENT DOCUMENTS

| EP | 1 418 523 A | 5/2004 |
| GB | 2443434 A | 5/2008 |

(Continued)

OTHER PUBLICATIONS

Evaluation of a New Measure of Blood Glucose Variability in Diabetes; BP Kovatchev, E Otto, D Cox, L Gonder-Frederick, W Clarke; Diabetes Care, vol. 29, No. 11, Nov. 2006.*

(Continued)

*Primary Examiner* — Michael Kahelin
*Assistant Examiner* — Karen Toth

(57) ABSTRACT

A diabetes management system or process is provided herein that may be used to analyze and recognize patterns for a large number of blood glucose concentration measurements and other physiological parameters related to the glycemia of a patient. In particular, a method of monitoring glycemia in a patient may include storing a patient's data on a suitable device, such as, for example, a blood glucose meter. The patient's data may include blood glucose concentration measurements. The diabetes management system or process may be installed on, but is not limited to, a personal computer, an insulin pen, an insulin pump, or a glucose meter. The diabetes management system or process may identify a plurality of pattern types from the data including a testing/dosing pattern, a hypoglycemic pattern, a hyperglycemic pattern, a blood glucose variability pattern, and a comparative pattern. After identifying a particular pattern with the data management system or process, a warning message may be displayed on a screen of a personal computer or a glucose meter. Other messages can also be provided to ensure compliance of any prescribed diabetes regiments or to guide the patient in managing the patient's diabetes.

3 Claims, 19 Drawing Sheets

(56) References Cited

U.S. PATENT DOCUMENTS

| | | | |
|---|---|---|---|
| 5,500,854 A | 3/1996 | Uotila | |
| 5,558,638 A | 9/1996 | Evers et al. | |
| 5,590,648 A | 1/1997 | Mitchell et al. | |
| 5,626,144 A | 5/1997 | Tacklind et al. | |
| 5,704,366 A | 1/1998 | Tacklind et al. | |
| 5,713,856 A | 2/1998 | Eggers et al. | |
| 5,772,586 A | 6/1998 | Heinonen et al. | |
| 5,822,715 A | 10/1998 | Worthington et al. | |
| 5,878,384 A | 3/1999 | Johnson et al. | |
| 5,925,021 A | 7/1999 | Castellano et al. | |
| 5,946,659 A | 8/1999 | Lancelot et al. | |
| 5,960,403 A | 9/1999 | Brown | |
| 5,974,389 A | 10/1999 | Clark et al. | |
| 5,997,476 A | 12/1999 | Brown | |
| 6,022,315 A | 2/2000 | Iliff | |
| 6,024,699 A | 2/2000 | Surwit et al. | |
| 6,049,764 A | 4/2000 | Stahl | |
| 6,081,786 A | 6/2000 | Barry et al. | |
| 6,134,504 A | 10/2000 | Douglas et al. | |
| 6,144,922 A | 11/2000 | Douglas et al. | |
| 6,188,988 B1 | 2/2001 | Barry et al. | |
| 6,206,829 B1 | 3/2001 | Iliff | |
| 6,225,901 B1 | 5/2001 | Kail, IV | |
| 6,234,964 B1 | 5/2001 | Iliff | |
| 6,270,455 B1 | 8/2001 | Brown | |
| 6,277,071 B1 | 8/2001 | Hennessy et al. | |
| 6,336,900 B1 | 1/2002 | Alleckson et al. | |
| 6,338,713 B1 | 1/2002 | Chamoun et al. | |
| 6,352,505 B1 | 3/2002 | Bortz | |
| 6,368,273 B1 | 4/2002 | Brown | |
| 6,379,301 B1 | 4/2002 | Worthington et al. | |
| 6,390,986 B1 | 5/2002 | Curcie et al. | |
| 6,406,426 B1 | 6/2002 | Reuss et al. | |
| 6,418,346 B1 | 7/2002 | Nelson et al. | |
| 6,422,061 B1 | 7/2002 | Sunshine et al. | |
| 6,450,956 B1 | 9/2002 | Rappaport et al. | |
| 6,524,240 B1 | 2/2003 | Thede | |
| 6,540,672 B1 | 4/2003 | Simonsen et al. | |
| 6,544,174 B2 | 4/2003 | West et al. | |
| 6,544,212 B2 | 4/2003 | Galley et al. | |
| 6,551,243 B2 | 4/2003 | Bocionek et al. | |
| 6,558,351 B1 | 5/2003 | Steil et al. | |
| 6,575,900 B1 | 6/2003 | Zweig et al. | |
| 6,579,231 B1 | 6/2003 | Phipps | |
| 6,604,050 B2 | 8/2003 | Trippel et al. | |
| 6,611,846 B1 | 8/2003 | Stoodley | |
| 6,635,016 B2 | 10/2003 | Finkelshteins | |
| 6,635,167 B1* | 10/2003 | Batman et al. | 205/775 |
| 6,645,142 B2 | 11/2003 | Braig et al. | |
| 6,656,114 B1 | 12/2003 | Poulsen et al. | |
| 6,692,436 B1 | 2/2004 | Bluth et al. | |
| 6,781,522 B2 | 8/2004 | Sleva et al. | |
| 6,799,149 B2 | 9/2004 | Hartlaub | |
| 6,804,558 B2 | 10/2004 | Haller et al. | |
| 6,872,200 B2 | 3/2005 | Mann et al. | |
| 6,915,170 B2 | 7/2005 | Engleson et al. | |
| 7,241,265 B2 | 7/2007 | Cummings et al. | |
| 2003/0216628 A1 | 11/2003 | Bortz et al. | |
| 2005/0119540 A1* | 6/2005 | Potts et al. | 600/315 |
| 2005/0159656 A1 | 7/2005 | Hockersmith et al. | |
| 2005/0187789 A1 | 8/2005 | Hatlestad et al. | |
| 2005/0214892 A1* | 9/2005 | Kovatchev et al. | 435/25 |
| 2005/0267780 A1 | 12/2005 | Ray et al. | |
| 2006/0010098 A1 | 1/2006 | Goodnow et al. | |
| 2006/0106644 A1 | 5/2006 | Koo et al. | |
| 2006/0173260 A1 | 8/2006 | Gaoni et al. | |
| 2006/0189863 A1 | 8/2006 | Peyser et al. | |
| 2006/0264895 A1 | 11/2006 | Flanders | |
| 2007/0033074 A1 | 2/2007 | Nitzan et al. | |
| 2008/0071580 A1 | 3/2008 | Marcus et al. | |
| 2008/0154513 A1* | 6/2008 | Kovatchev et al. | 702/19 |
| 2008/0234943 A1 | 9/2008 | Ray et al. | |
| 2008/0234992 A1 | 9/2008 | Ray et al. | |
| 2008/0235053 A1 | 9/2008 | Ray et al. | |
| 2008/0255438 A1* | 10/2008 | Saidara et al. | 600/365 |
| 2009/0105573 A1* | 4/2009 | Malecha | 600/365 |
| 2009/0171589 A1 | 7/2009 | Kovatchev | |
| 2009/0240127 A1* | 9/2009 | Ray | 600/365 |
| 2010/0332445 A1* | 12/2010 | Ray et al. | 706/54 |

FOREIGN PATENT DOCUMENTS

| | | |
|---|---|---|
| JP | H4-348747 | 12/1992 |
| JP | 2001-245900 | 9/2001 |
| JP | 2002-132952 | 5/2002 |
| JP | 2003-500744 A | 1/2003 |
| JP | 2004-024699 | 1/2004 |
| JP | 2004-154547 | 6/2004 |
| WO | WO 00/04512 A | 1/2000 |
| WO | WO 01/00086 | 1/2001 |
| WO | 02/05702 A2 | 1/2002 |
| WO | 02/15777 A1 | 2/2002 |
| WO | WO02/15777 * | 2/2002 |
| WO | 2005/065538 A2 | 7/2005 |
| WO | 2005/081170 A2 | 9/2005 |
| WO | WO 2005/093629 A | 10/2005 |
| WO | WO 2007/005170 A | 1/2007 |
| WO | WO 2008/071218 A1 | 6/2008 |

OTHER PUBLICATIONS

Statistical Hypoglycemia Prediction; F Cameron, G Niemeyer, K Gundy-Burlet, B Buckingham; J Diabetes ZSi Technol. 008 Jul.; 2(4): 612-621.*

European Search Report, EP application No. 08250986.0, dated Jan. 28, 2009, 6 pages.

Michael Browlee, et al., "Glycemic Variability: A Hemoglobin A1c-Independent Risk Factor for Diabetic Complications", JAMA, Apr. 12, 2006, pp. 1707-1708, vol. 295, No. 14.

Irl B. Hirsch, M.D., "Glycemic Variability: It's Not Just About A1C Anymore!", Diabetes Technology & Therapeutics, 2005, pp. 780-783, vol. 7, No. 5.

Boris P. Kovatchev, et al., "Evaluation of a New Measure of Blood Glucose Variability in Diabetes", Diabetes Care, Nov. 2006, pp. 2433-2438, vol. 29, No. 11.

Boris P. Kovatchev, et al., "Methods for Quantifying Self-Monitoring Blood Glucose Profiles Exemplified by an Examination of Blood Glucose Patterns in Patients with Type 1 and Type 2 Diabetes", Diabetes Technology & Therapeutics, 2002, pp. 295-303, vol. 4, No. 3.

Louis Monnier, et al., "Activation of Oxidative Stress by Acute Glucose Fluctuations Compared with Sustained Chronic Hyperglycemia in Patients with Type 2 Diabetes", JAMA, Apr. 12, 2006, pp. 1681-1687, vol. 295, No. 14.

David Rodbard, "Improved Methods for Calculating a "Figure of Merit" for Blood Glucose Monitoring Data", Diabetes Technology Meeting, San Francisco, CA Nov. 2005, 1 page.

Edmond A. Ryan, et al., "Assessment of the Severity of Hypoglycemia and Glycemic Lability in Type 1 Diabetic Subjects Undergoing Islet Transplantation", Diabetes, Apr. 2004, pp. 955-962, vol. 53.

J.M. Wojcicki, ""J"-Index. A New Proposition of the Assessment of Current Glucose Control in Diabetic Patients", Hormone and Metabolic Research, 1995, pp. 41-42, vol. 27.

Department of Health and Human Services, Public Health Service, Food and Drug Administration Center for Devices and Radiological Health; Roche Diagnostics Corp. 510(k) No. K043529; ACCU-CHEK Advisor Insulin Guidance Software Mar. 31, 2005; 1201 pages.

European Search Report, EP Application No. 08251030.6, Munich, Germany dated Feb. 12, 2009, 10 pages.

F. John Service, M.D., et al., "Mean Amplitude of Glycemic Excursions, a Measure of Diabetic Instability", Diabetes, vol. 19, No. 9, Sep. 1970, 644-655.

J. Schlichtkrull, et al., "The M-Value, an Index of Blood-sugar Control in Diabetics", Acta Medica Scandinavica, vol. 177, fast. 1, 1965, 95-102.

David Rodbard, M.D., "Optimizing Display, Analysis, Interpretation and Utility of Self-Monitoring of Blood Glucose (SMBG) Data for

(56) References Cited

OTHER PUBLICATIONS

Management of Patients with Diabetes", Journal of Diabetes Science and Technology, vol. 1, Issue 1, Jan. 2007, 62-71.

Accu-Chek Camit Pro User's Manual, Roche Diagnostics, 2005, 220 pages.

Japanese Patent Application No. 2008-063000, Notice of Reasons for Rejection mailed Sep. 4, 2012, Japanese Patent Office, 3 pages.

Adil Alaoui, M.S., et al., "Diabetes Home Monitoring Project," ISIS Center, Department of Radiology, Georgetown University Medical Center, Nov. 12, 1998, pp. 2-6.

M. Berger, et al., "Computer Programs to Assist the Physician in the Analysis of Self-Monitored Blood Glucose Data," Proc. Annu. Symp. Comput. Appl. Med. Care, vol. 9, Nov. 1988, pp. 52-57.

M.P. Berger, et al., "Combining Statistical, Rule-Based, and Physiologic Model-Based Methods to Assist in the Management of Diabetes Mellitus," Computers and Biomedical Research, vol. 23, 1990, pp. 346-357.

Bruce W. Bode, et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.

E.J. Gomez-Aguilera, et al., "Diacrono: A New Portable Microcomputer System for Diabetes Management," IEEE/Ninth Annual Conference of the Engineering in Medicine and Biology Society—1231, 1987, 2 pages.

E.J. Gomez, et al., "Telemedicine for Diabetes Care: the DIABTel Approach Towards Diabetes Telecare," Med. Inform., vol. 21, No. 4, 1996, pp. 283-295.

M.E. Hernando, et al., "DIABNET: A Qualitative Model-Based Advisory System for Therapy Planning in Gestational Diabetes," Med. Inform., vol. 21, No. 4, 1996, pp. 359-374.

Jacob Jaremko, et al., "Advances Toward the Implantable Artificial Pancreas for Treatment of Diabetes," Diabetes Care, vol. 21, No. 3, Mar. 1998, pp. 444-450.

N. Pernick, et al., "A Microcomputer Consultation System for Self-Adjustment of Insulin Dosage," The American Association for Medical Systems and Informatics, vol. 2, 1983, pp. 62-67.

N. Pernick, et al., "Personal Computer Programs to Assist with Self-Monitoring of Blood Glucose and Self-Adjustment of Insulin Dosage," Diabetes Care, vol. 9, No. 1, Jan.-Feb. 1986, pp. 61-69.

K. Rebrin, et al., "Subcutaneous Glucose Monitoring by Means of Electrochemical Sensors: Fiction or Reality?," J. Biomed. Eng., vol. 14, Jan. 1992, pp. 33-41.

Japanese Patent Application No. 2008-063023, Notice of Reasons for Rejection mailed Dec. 18, 2012, Japanese Patent Office, 2 pages.

Japanese Patent Application No. 2008-62994, Notice of Reasons for Rejection mailed Apr. 9, 2013, Japanese Patent Office, 3 pages.

European Patent Application No. 11181876.1, extended European Search Report mailed Jun. 14, 2013, European Patent Office, 9 pages.

European Patent Application No. 11181875.3, extended European Search Report mailed Jun. 18, 2013, European Patent Office, 10 pages.

Wintergerst, K.A., et al., "Association of Hypoglycemia, Hyperglycemia, and Glucose Variability with Morbidity and Death in the Pediatric Intensive Care Unit," Pediatrics, vol. 118, No. 1, Jul. 2006, pp. 173-179.

\* cited by examiner

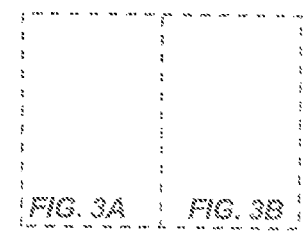
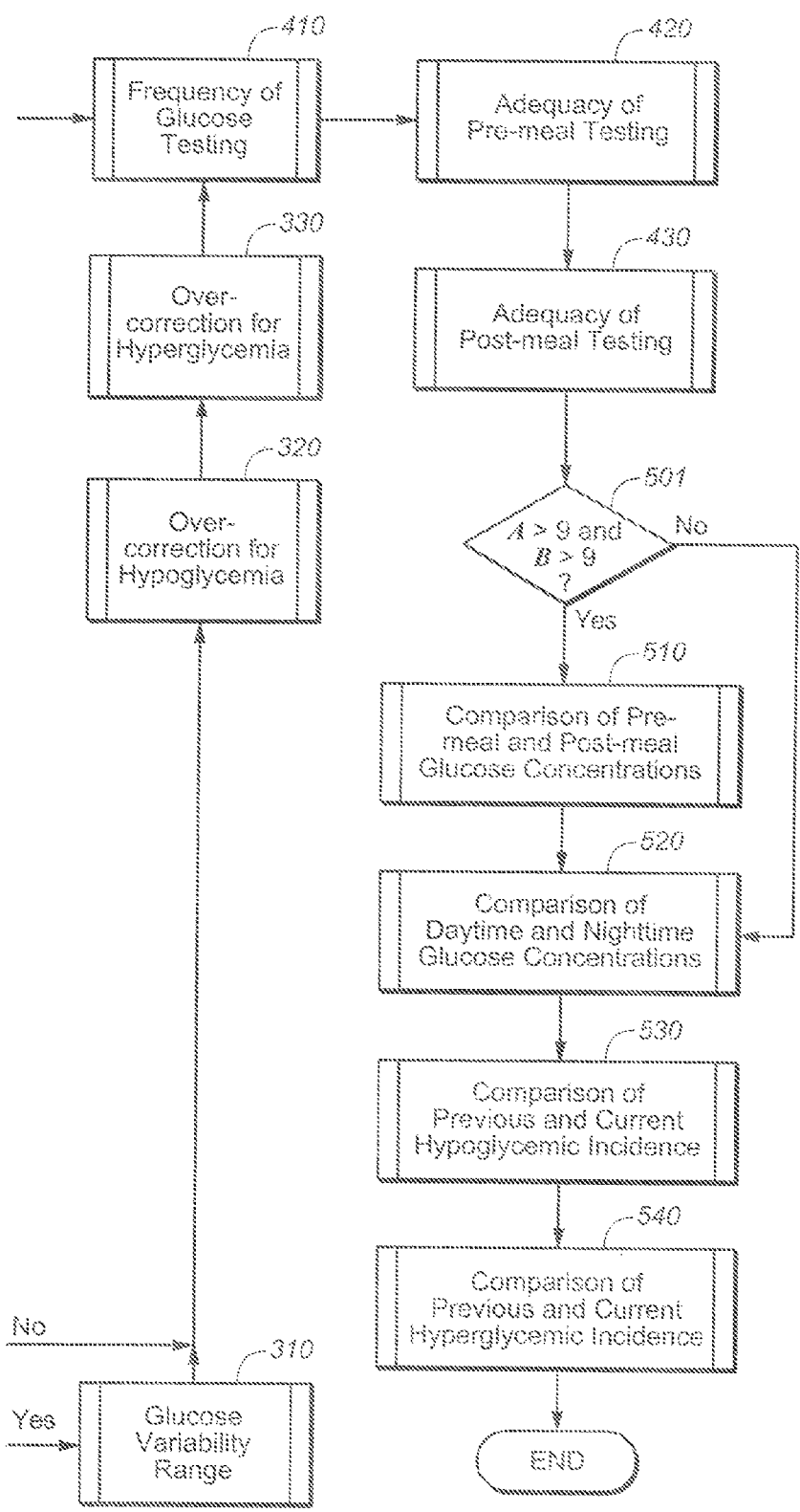
FIG. 3B

FIG. 4C

| | Outcome 1 (e.g., Hypoglycemic) | | Outcome 2 (e.g., Not Hypoglycemic) | | Row Total | SE | Z test |
|---|---|---|---|---|---|---|---|
| | Observed | Expected | Observed | Expected | | | |
| Condition 1 (e.g., day of week) | $L_1$ | $L_{1,pre} = \dfrac{\sum_{i=1}^{n} L_i}{\sum_{i=1}^{n} N_i} * N_1$ | $L'_1$ | $L'_{1,pre} = \dfrac{\sum_{i=1}^{n} L'_i}{\sum_{i=1}^{n} N_i} * N_1$ | $N_1 = L_1 + L'_1$ | $SE_1 = \sqrt{\dfrac{1}{N_1} * L_{1,pre} * (N_1 - L_{1,pre})}$ | $Z_1 = \dfrac{(L_1 - L_{1,pre})}{SE_1}$ |
| Condition 2 | $L_2$ | $L_{2,pre} = \dfrac{\sum_{i=1}^{n} L_i}{\sum_{i=1}^{n} N_i} * N_2$ | $L'_2$ | $L'_{2,pre} = \dfrac{\sum_{i=1}^{n} L'_i}{\sum_{i=1}^{n} N_i} * N_2$ | $N_2 = L_2 + L'_2$ | $SE_2 = \sqrt{\dfrac{1}{N_2} * L_{2,pre} * (N_2 - L_{2,pre})}$ | $Z_2 = \dfrac{(L_2 - L_{2,pre})}{SE_2}$ |
| Condition 3 | $L_3$ | $L_{3,pre} = \dfrac{\sum_{i=1}^{n} L_i}{\sum_{i=1}^{n} N_i} * N_3$ | $L'_3$ | $L'_{3,pre} = \dfrac{\sum_{i=1}^{n} L'_i}{\sum_{i=1}^{n} N_i} * N_3$ | $N_3 = L_3 + L'_3$ | $SE_3 = \sqrt{\dfrac{1}{N_3} * L_{3,pre} * (N_3 - L_{3,pre})}$ | $Z_3 = \dfrac{(L_3 - L_{3,pre})}{SE_3}$ |
| ...... | ...... | ...... | ...... | ...... | ...... | ...... | ...... |
| Condition $n$ | $L_n$ | $L_{n,pre} = \dfrac{\sum_{i=1}^{n} L_i}{\sum_{i=1}^{n} N_i} * N_n$ | $L'_n$ | $L'_{n,pre} = \dfrac{\sum_{i=1}^{n} L'_i}{\sum_{i=1}^{n} N_i} * N_n$ | $N_n = L_n + L'_n$ | $SE_n = \sqrt{\dfrac{1}{N_n} * L_{n,pre} * (N_n - L_{n,pre})}$ | $Z_n = \dfrac{(L_n - L_{n,pre})}{SE_n}$ |

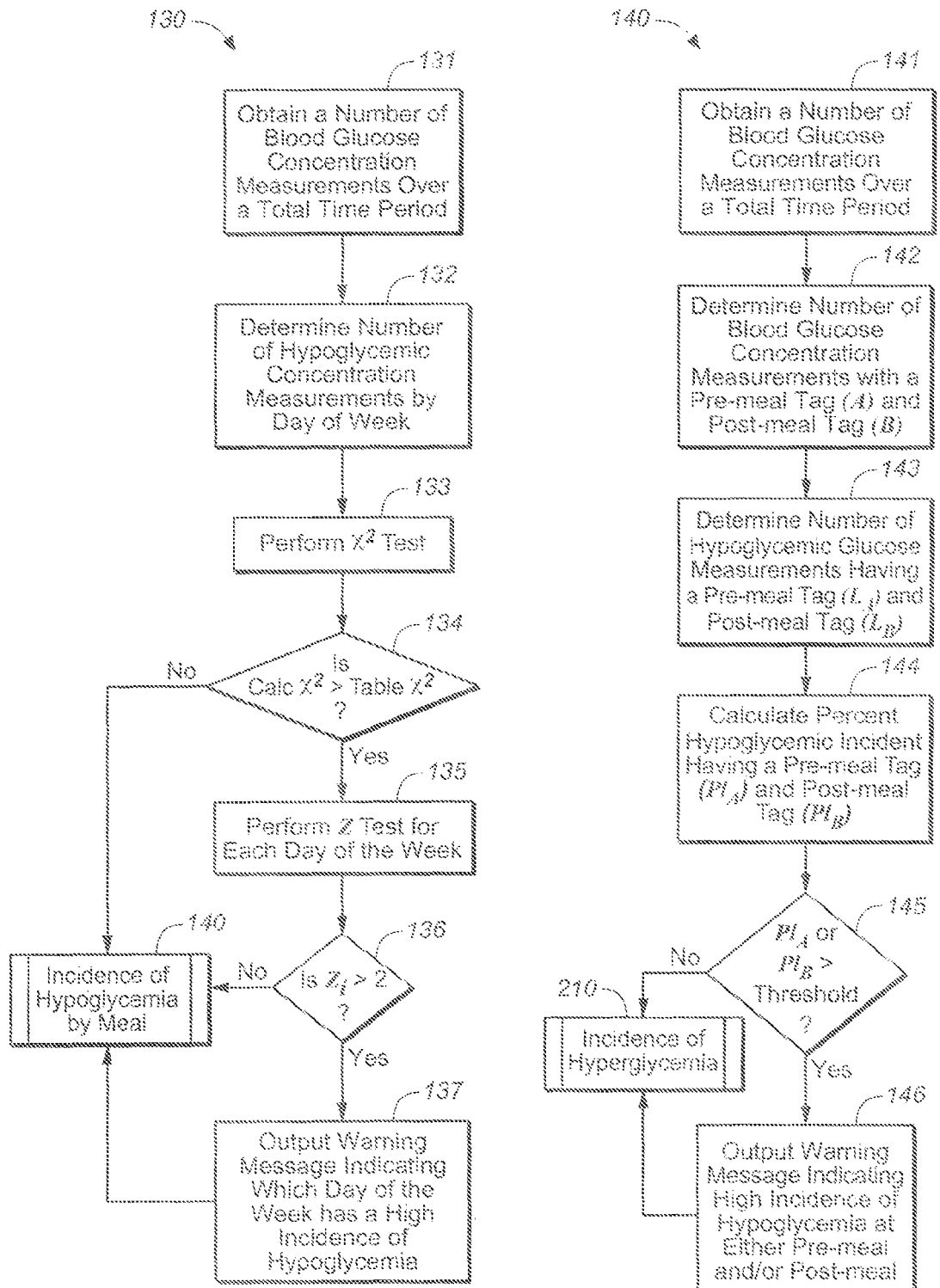

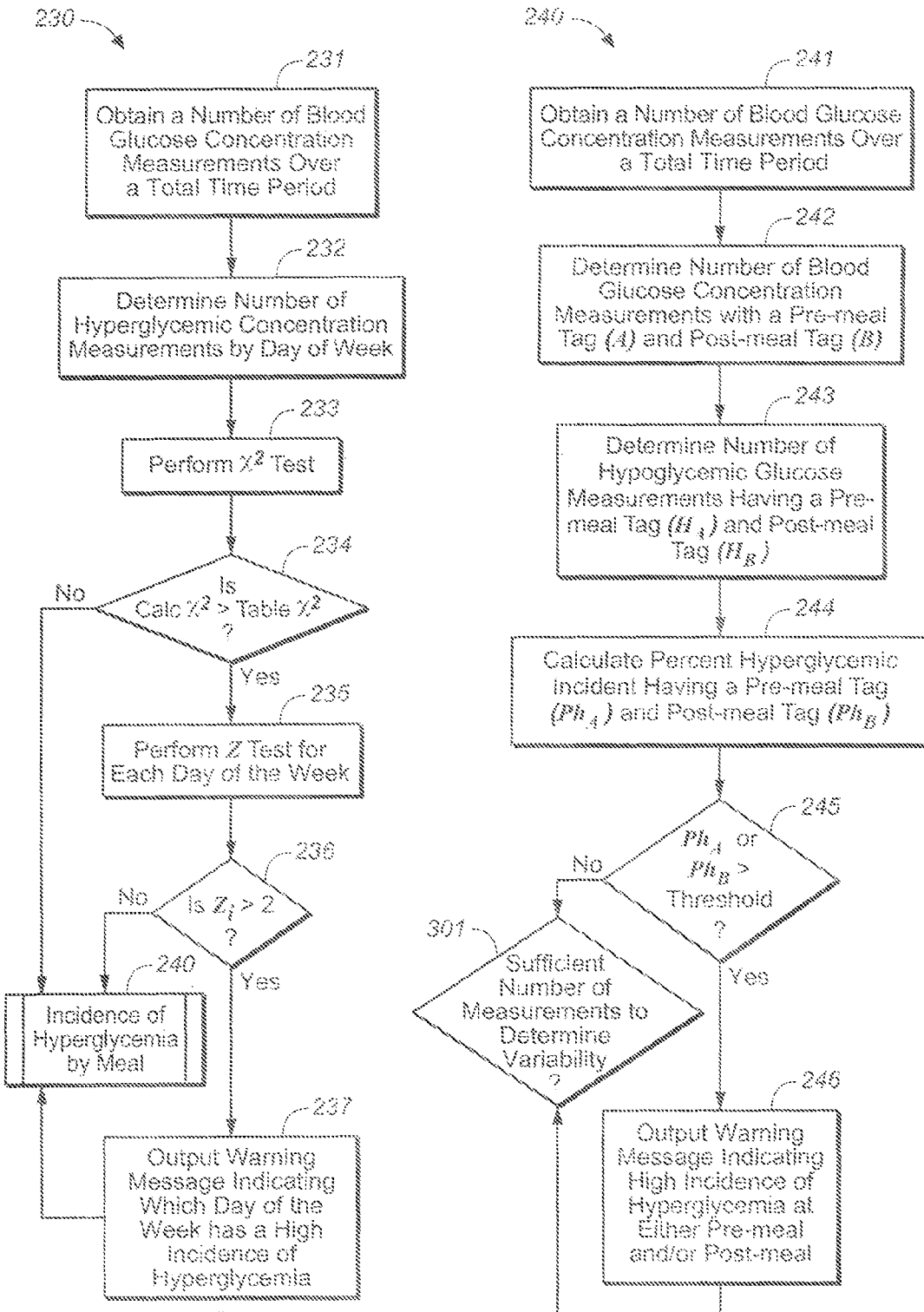

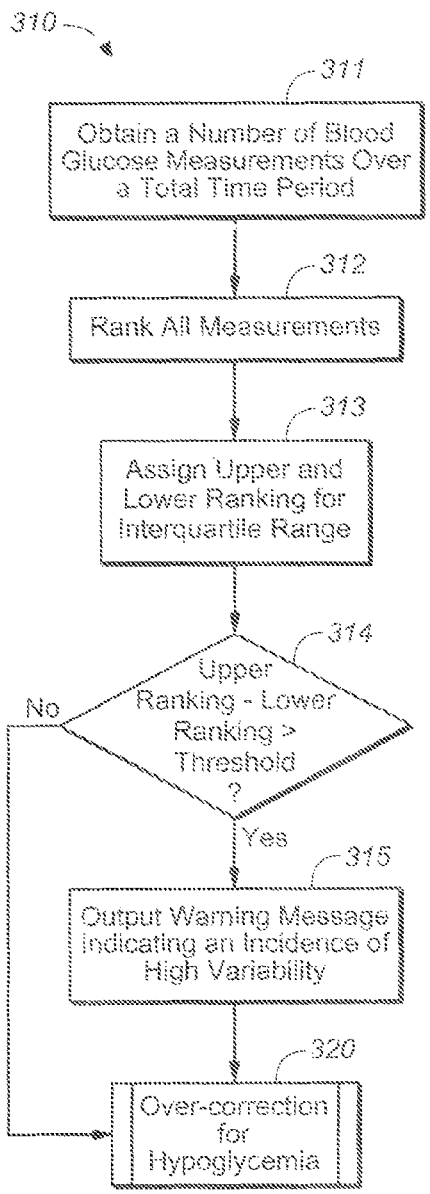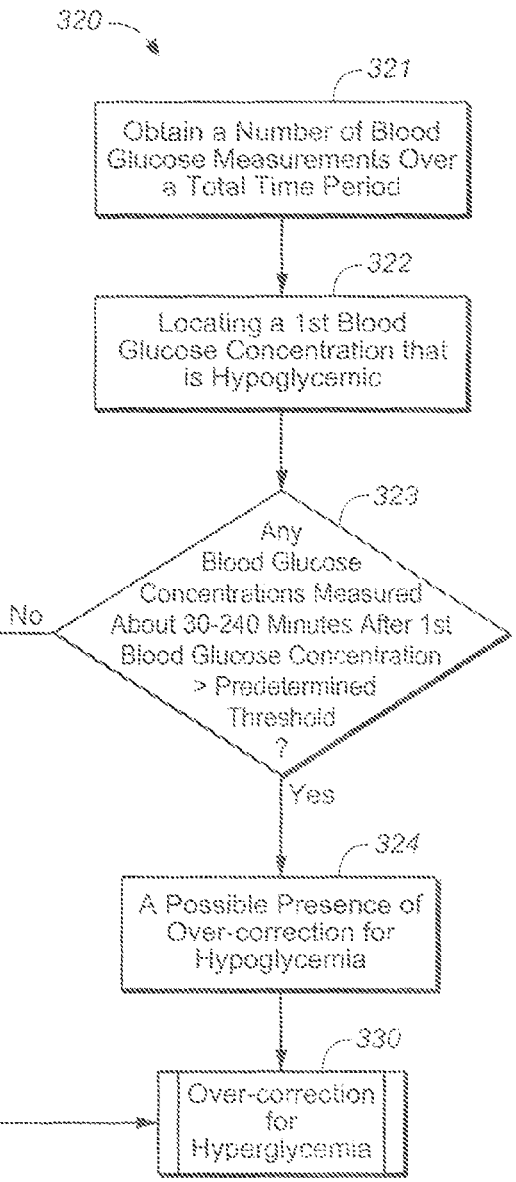
FIG. 10                              FIG. 11

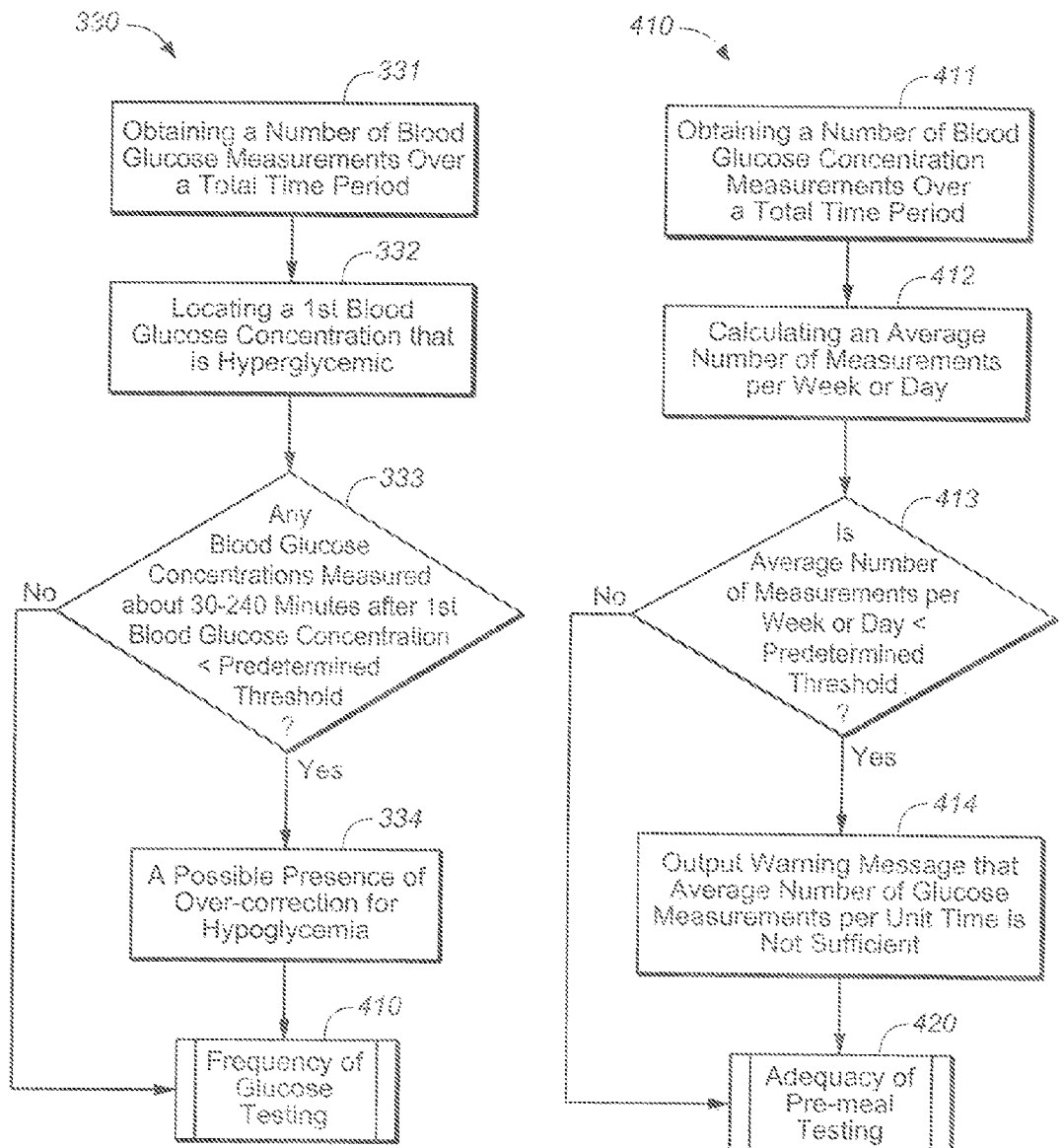

FIG. 19A

PATIENT SUMMARY (5/11/2006 - 6/9/2006)

Patient: Doe, Jane
Date of Birth (Gender): (Female)
Date Range: 5/11/2006 - 6/9/2006

Pre-meal Target: 70 - 110 mg/dL (Plasma)
Post-meal Target: 90 - 140 mg/dL (Plasma)
Hypo. Threshold: 69 mg/dL (Plasma)
Hyper. Threshold: 160 mg/dL (Plasma)

Goals for Diabetes [to be filled out by physician]

| | Guideline | Latest Values (Date) | Goal |
|---|---|---|---|
| HbA1c | Less than or equal to 6.5% | | |
| Blood Pressure | Less than 130/80 mmHg | | |
| Cholesterol | LDL: Less than 100 mg/dL | | |
| Weight | Physician Recommends | | |

Additional Comments

Diet and Exercise:

Other:

Medication:

SYSTEMS AND METHODS FOR PATTERN RECOGNITION IN DIABETES MANAGEMENT

This application claims the benefits of U.S. patent application Ser. No. 11/688,768, filed on Mar. 20, 2007, which application is hereby incorporated by reference in its entirety into this application. The present invention is related to U.S. patent application Ser. No. 11/688,743, filed on Mar. 20, 2007, now abandoned.

People with diabetes often rely upon the use of blood glucose meter in conjunction with help from their physicians for managing their disease. In addition, people with diabetes typically use a logbook to keep track of their glucose concentration measurements. Under certain circumstances, interpreting a large number of glucose concentration measurements in a logbook format can be difficult, complex, and time consuming. To further complicate matters, physicians usually have limited time constraints in assisting people with diabetes to interpret a large number of glucose concentration measurements. When such complication with blood glucose values is further compounded by the need to assess the effect of insulin or type of insulin, and other physiological parameters or external parameters, it is believed that the task of the clinician, physician or person with diabetes is made even more difficult. An additional hurdle for physicians or clinicians is the time constraint placed upon an office visit for the patient due to the economics of running a medical office. It is believed that in most cases, a physician or clinician typically spends less than approximately seven (7) minutes per patient, which results in little or no time for assessment or guidance for the patient. Applicants have recognized the need to allow for simple and quick assessment of glycemic trends, patterns, data, and graphical correlation of important blood glucose and other physiological or external parameters by a busy physician, clinician, and the patient.

SUMMARY

In one aspect, a diabetes management system or process is provided herein that may be used to analyze and recognize patterns for a large number of glucose concentration measurements and other physiological or external parameters related to the glycemia of a patient. In particular, a method of monitoring glycemia in a patient may include storing a patient's data on a suitable device, such as, for example, a glucose meter. The patient's data may include blood glucose concentration measurements. The diabetes management system or process may be installed on, but is not limited to, a personal computer, an insulin pen, an insulin pump, or a glucose meter. The diabetes management system or process may identify a plurality of pattern types from the data including a testing/dosing pattern, a hypoglycemic pattern, a hyperglycemic pattern, a blood glucose variability pattern, and a comparative pattern. After identifying a particular pattern with the data management system or process, a warning message may be displayed on a screen of a personal computer or a glucose meter. Other messages can also be provided to ensure compliance of any prescribed diabetes regiments or to guide the patient in managing the patient's diabetes.

In particular, a method of monitoring glycemia in a patient is provided. The method can be achieved by storing a patient's data that includes blood glucose concentration measurements; generating a plurality of patterns including multiple blood glucose variability patterns; and displaying at least one of the multiple blood glucose variability patterns over a predetermined time period.

In yet another embodiment, a method of monitoring glycemia in a patient is provided. The method can be achieved by storing a patient's data that includes blood glucose concentration measurements; generating statistically significant patterns from the patient's data, the patterns indicative of hypoglycemia, hyperglycemia, or excessive blood glucose variability by time of day, by day in a week, both by time of day and day of week, or at different time intervals; calculating standard error and Z test with data from the table; and displaying a message upon the Z test is greater than a predetermined value indicative of a pattern of glycemia outside at least a predetermined range for such pattern.

These and other embodiments, features and advantages will become apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which:

FIGS. 3A and 3B illustrate a flow chart of the diabetes management system or process system;

FIG. 4C illustrates an exemplary chi-squared table that can be used to determine statistically significant patterns based on a patient's data.

FIG. 5 illustrates a flow chart for analyzing a plurality of glucose concentration measurements for a pattern that may indicate a hypoglycemic pattern by day of week;

FIG. 6 illustrates a flow chart for analyzing a plurality of glucose concentration measurements for a pattern that may indicate an incidence of hypoglycemia by meal;

FIG. 8 illustrates a flow chart for analyzing a plurality of glucose concentration measurements for a pattern that may indicate a hyperglycemic pattern by day of week;

FIG. 9 illustrates a flow chart for analyzing a plurality of glucose concentration measurements for a pattern that may indicate an incidence of hyperglycemia by meal;

FIG. 10 illustrates a flow chart for analyzing a plurality of glucose concentration measurements for a pattern that may indicate an incidence of high blood glucose variability;

FIG. 11 illustrates a flow chart for analyzing a plurality of glucose concentration measurements for a pattern that may indicate an overcorrection for hypoglycemia;

FIG. 12 illustrates a flow chart for analyzing a plurality of glucose concentration measurements for a pattern that may indicate an overcorrection for hyperglycemia;

FIG. 13 illustrates a flow chart for analyzing a plurality of glucose concentration measurements for a pattern that may indicate whether the frequency of glucose testing is sufficient;

FIGS. 19A and 19B illustrate a patient information sheet that was generated using an embodiment of the diabetes management system.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will enable one skilled in the art to make and use the invention, and describes several embodiments, adaptations, variations, alternatives and uses of the invention, including what is presently believed to be the best mode of carrying out the invention.

Figure 1:
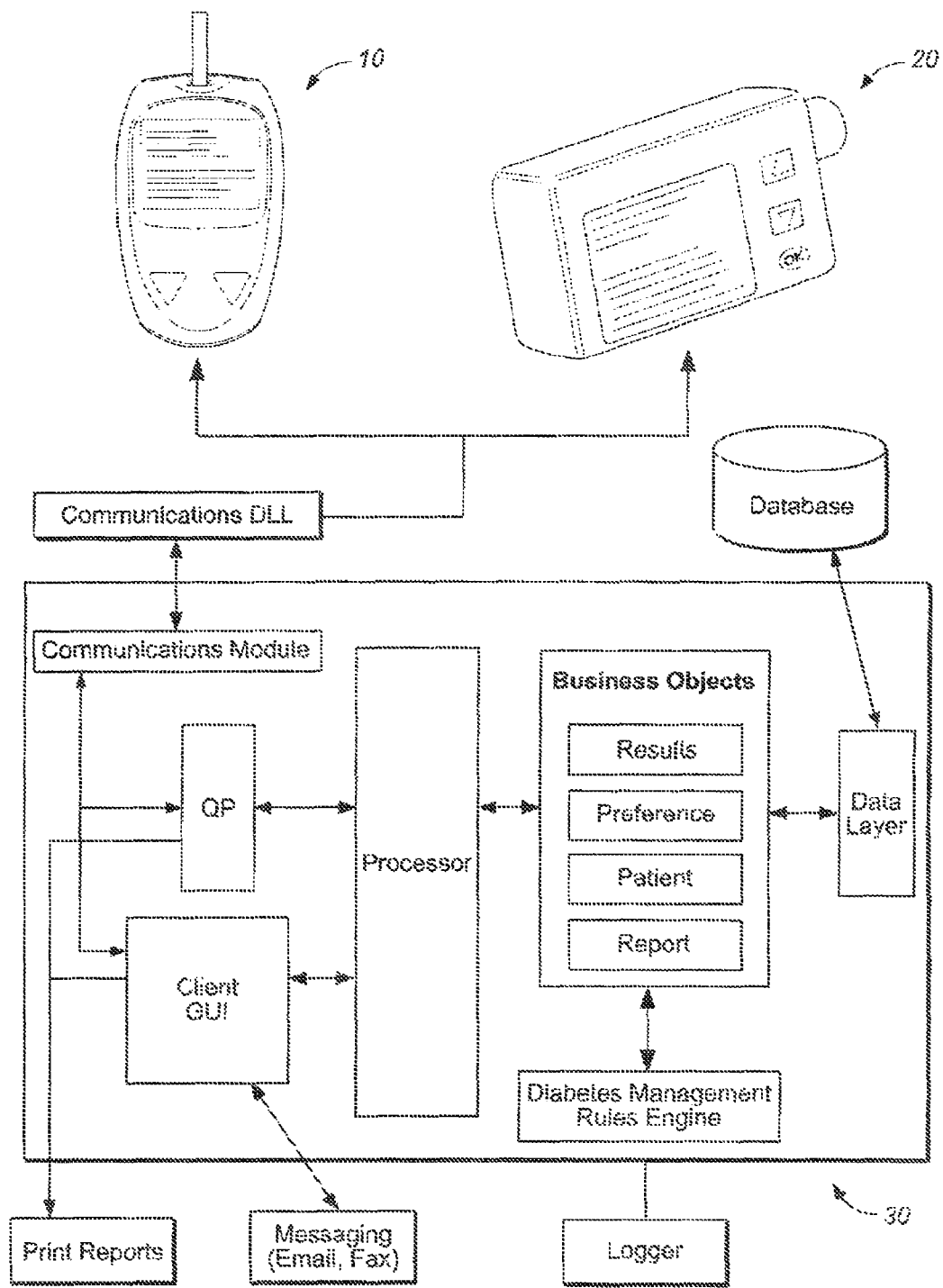
FIG. 1 illustrates a schematic of a diabetes management system that includes a glucose meter, an insulin pump, and a personal computer.

FIG. 1 illustrates a schematic of a diabetes management system that includes a glucose meter 10, an insulin pump 20, and a personal computer (PC) 30. PC 30, illustrated in schematic form in FIG. 1, may have a microprocessor unit and a memory unit. Glucose meter 10 may be configured to use a disposable test strip having a reagent such as, for example, glucose oxidase, ferricyanide, ruthamine hexamine, or combinations thereof. The reagent chemistry is capable of a physical transformation of glucose that allows a signal to be measured with glucose meter 10. In one embodiment, a diabetes management system or process may be installed on the memory unit in PC 30. In another embodiment, the diabetes management system or process may be installed on a memory unit of glucose meter 10, insulin pump 20, or other suitable computing device such as a personal digital assistant (PDA) or a cellular phone, i.e., any communication device with a processor and graphical user interface with a visual or audio output.

Glucose meter 10, insulin pump 20, and PC 30 may all have the ability to bi-directionally transfer data to each other. The data transfer process may be implemented in a wired or wireless manner. A cable may be used to transfer data in a wired manner through a suitable wire medium such as, for example, a universal serial bus (USB), serial port (RS232) or application specific connectors. The data transfer process may also use a suitable wireless medium with a wireless protocol such as, for example, infrared (IR), radio frequency (RF), WiFi (IEEE 802.11 wireless Ethernet standards), and Bluetooth or application specific wireless protocol.

Diabetes management system or process may include a communications dynamic link library (DLL), a communications module, a quick print module QP, a graphical user interface (GUI), business object module, a diabetes management rules engine, a data layer module, and a database module, as illustrated in FIG. 1. Diabetes management system or process may be configured to generate reports, print reports, send reports via e-mail and fax, and to log errors via the logger, as illustrated in FIG. 1.

The communications DLL may be an executable program module that allows PC 30 to recognize and communicate with glucose meter 10 and insulin pump 20. In addition, the communications DLL may allow PC 30 to communicate with several different types of glucose meters and insulin pumps and also a wide array of devices such as scales, sphygmomanometer, thermometers, pedometers, and heart rate monitors. The communication module may act as a surrogate by abstracting the lower level functionality that establishes connectivity with serial and USB devices.

The quick print module QP may be a sub-routine configured to cause a glucose meter to seamlessly transfer data to PC 30 and then print a data report. After an initial setup, glucose meter 10 may be connected to PC 30 with a cable. Without having to manually launch a management application or perform any additional steps, the glucose meter will transfer its data and then print the data report. Details of the quick print module QP are shown and described in U.S. patent application Ser. No. 11/142,903 filed on May 31, 2005, which is incorporated by reference in its entirety herein.

The GUI may be a plurality of user interface screens that allow a user to configure and operate the diabetes management system or process. The screens can be configured as a touch screen or a combination of a display and a keyboard or buttons.

The business object module may be a central engine that will integrate and communicate with types of results, patient, preference, and reporting functionalities. The business object rules may be used by the GUI to generate results, reports, or other functionalities. As used herein, the term "patient" includes not only human subjects but also other mammals with indication of diabetes.

The data layer module may be an abstracted data access layer, which may act as an intermediate layer between the database module and the management application. The data layer module may execute the queries on the database module and return a record set, if applicable.

The database module may be a tool for storing and organizing data collected from glucose meter 10 and alternatively other devices. The database module may be installed, for example, on PC 30, a network server or transportable memory storage device.

The diabetes management rule engine may include a plurality of processes, devices, or sub-routines for analyzing data from glucose meter 10 and/or insulin pump 20. The plurality of sub-routines may apply statistical tests and triggers to analyze data so that messages can be provided to a user and/or a physician to warn about possible problem spots and/or compliance issues. A microprocessor may be configured to analyze data using the diabetes management rule engine. The diabetes management rule engine may be configurable by a physician and/or a user.

Figure 2:
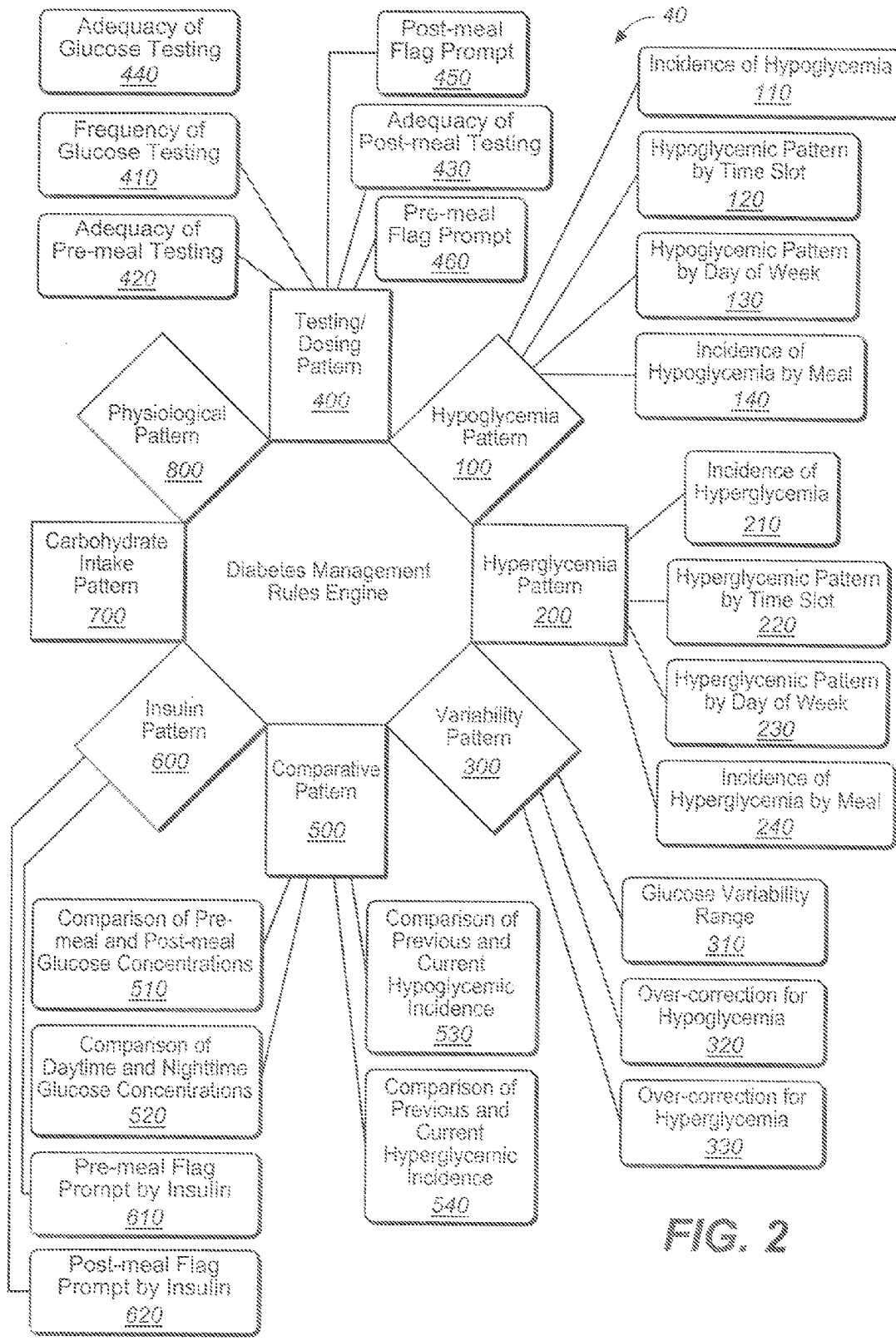
FIG. 2 illustrates a schematic of a diabetes management rules engine.

In one embodiment, the diabetes management rule engine may include a plurality of pattern recognition rules that can identify a testing/dosing pattern 400, a hypoglycemic pattern 100, a hyperglycemic pattern 200, a blood glucose variability pattern 300, a comparative pattern 500, and an insulin pattern 600, as illustrated in FIG. 2. The testing/dosing pattern 400 may include the following sub-routines, such as, for example, a frequency of glucose testing 410, an adequacy of pre-meal testing 420, an adequacy of post-meal testing 430, an adequacy of glucose testing 440, a post-meal flag prompt 450, and a pre-meal flag prompt 460. The hypoglycemic pattern 100 may include the following sub-routines, such as, for example, an incidence of hypoglycemia 110, a hypoglycemic pattern by time slot 120, a hypoglycemic pattern by day of week 130, and an incidence of hypoglycemia by meal 140. The hyperglycemic pattern 200 may include the following sub-routines such as, for example, an incidence of hyperglycemia 210, a hyperglycemic pattern by time slot 220, a hyperglycemic pattern by day of week 230, and an incidence of hyperglycemia by meal 240. The blood glucose variability pattern 300 may include the following sub-routines such as, for example, a glucose variability range 310, an overcorrection for hypoglycemia 320, and an overcorrection for hyperglycemia 330. The comparative pattern 500 may include the following sub-routines such as, for example, a comparison of pre-meal and post-meal glucose concentrations 510, a comparison of daytime versus nighttime glucose concentrations 520, a comparison of previous and current hypoglycemic incidence 530, and a comparison of previous and current hyperglycemic incidence 540.

Alternatively, the plurality of pattern recognition rules may include an insulin pattern 600, a carbohydrate intake pattern 700 and a physiological pattern 800. The insulin pattern 600 may include the following sub-routines such as, for example, a pre-meal flag prompt by insulin 610 and a post-meal flag prompt by insulin 620.

The following will describe a description of the aforementioned pattern recognition rules (100, 200, 300, 400, 500, and 600).

Figure 3A:
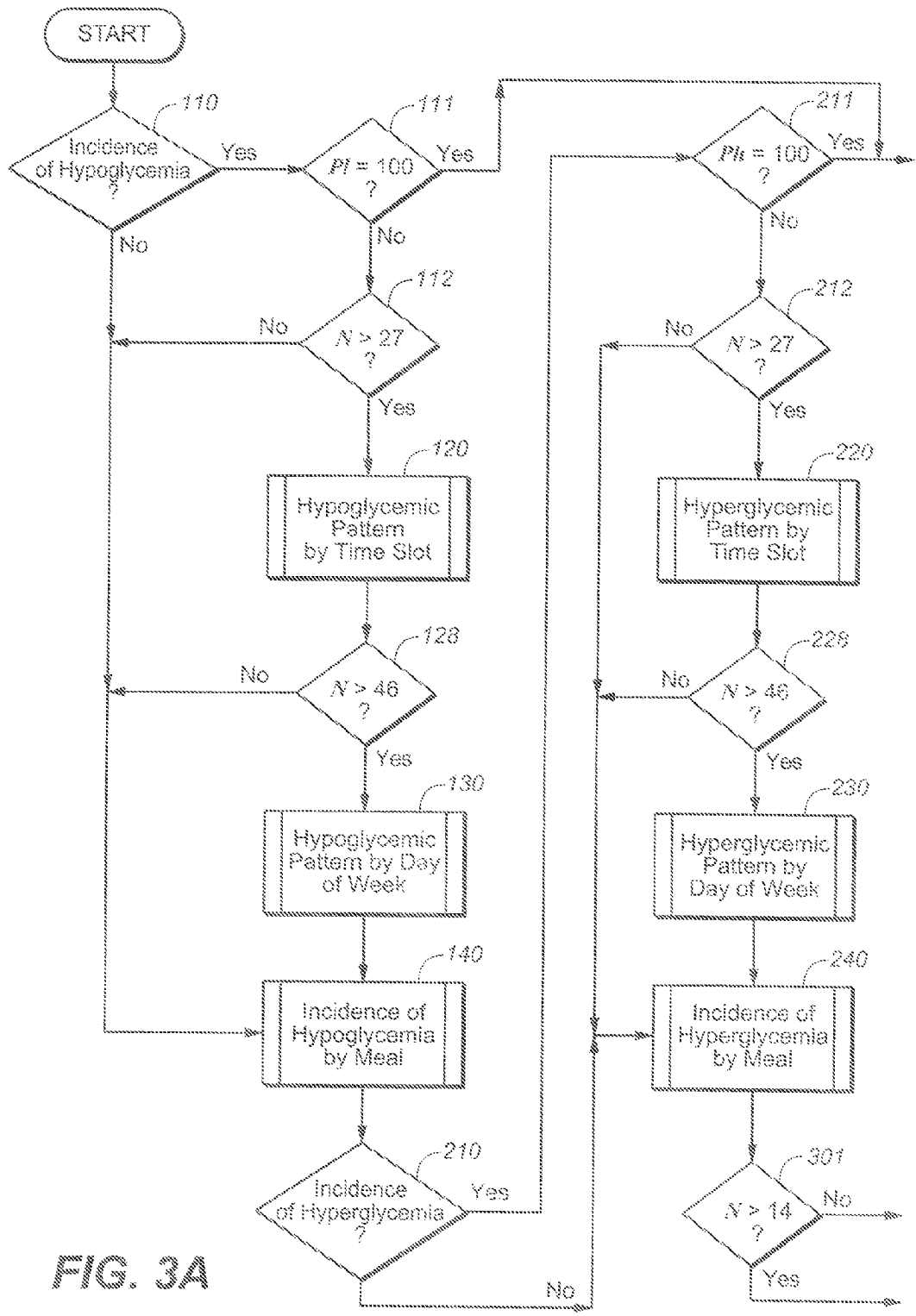

FIGS. 3A and 3B illustrate a flow chart of the diabetes management system or process system. A plurality of glucose concentration measurements may be processed using incidence of hypoglycemia sub-routine 110. If the percentage of hypoglycemic incidence Pl is greater than a predetermined threshold, then the method moves to step 111 to determine whether the percentage of hypoglycemic incidence Pl equals about 100%. If the percentage of hypoglycemic incidence Pl in step 110 is less than a pre-determined threshold, then the method moves to the incidence of hypoglycemia by meal sub-routine 140. The pre-determined threshold for the incidence of hypoglycemia sub-routine 110 may range from about 3% to about 15%. In the preferred embodiment, the threshold is about 5%. Alternatively, the threshold may be of any value as selected by a clinician or physician. And as used herein, the term "about" or "approximately" in conjunction with a numerical value denotes that variations in the numerical value are intended as long as the variations allow the exemplary embodiments to perform for its intended purpose.

For step 111, if the hypoglycemic frequency Pl equals about 100%, then the method moves to the frequency of glucose testing sub-routine 410. However, if the hypoglycemic frequency Pl in step 111 does not equal about 100%, then the method moves to step 112 to determine whether more than about 27 glucose concentration measurements have been collected.

For step 112, if there are more than about 27 measurements, then the method moves to the hypoglycemic pattern by time slot sub-routine 120. However, if there are not more than about 27 measurements, then the method moves to the incidence of hypoglycemia by meal sub-routine 140. The sample size of 27 represents approximately the minimum number of glucose measurements required to perform sub-routine 120 and is based on several assumptions including: that a user tests at least once per day; that a user tests in at least two times per day; that there are at least two categories of observed incidences that are hypoglycemic incidences and not hypoglycemic incidences; and that the at least two categories each have greater than or equal to about five incidences. When using a chi-squared test, the minimum expected number of incidences is five for each category per time slot. Thus, two-time slots times two categories times five expected number of incidences gives approximately a minimum sample size of twenty. Based on the calculations, the sample size may be greater than about 20, and preferably be greater than about 27. For sample sizes greater than 20 such as, for example, 27 can be desirable based on a balancing test between consumer expectations of having the capability of receiving accurate warnings about their glycemic patterns without having to do an excessive number of glucose measurements, and having a sufficient number of glucose measurement to ensure a relative low number of false positive and false negative results.

The hypoglycemic pattern by time slot sub-routine 120 is performed if more than about 27 glucose concentration measurements were found in step 112. After performing the hypoglycemic pattern by time slot sub-routine 120, the method determines whether the plurality of glucose concentration measurements has more than about 46 measurements, as shown in step 128. If more than about 46 glucose concentration measurements have been collected, as shown in step 128, then the method moves to the hypoglycemic pattern by day of week sub-routine 130 and also to the incidence of hypoglycemia by meal sub-routine 140. If not more than about 46 glucose concentration measurements have been collected, as indicated in step 128, then the method moves to the incidence of hypoglycemia by meal sub-routine 140. The sample size of 46 measurements is based on several assumptions that include that a user tests at least once per day; that the user tests in at least five of the seven days per week; that there are at least two categories of observed incidences that are hypoglycemic incidences and not hypoglycemic incidences; and that the at least two categories each have greater than or equal to about five incidences for the at least five days of the week. When using a chi-squared test, the minimum expected number of incidences is five for each category per day of the week. Thus, five days times two categories times five expected counts gives a minimum sample size of 50. Based on the calculations, the sample size may be greater than about 50, and preferably be greater than about 46. For sample sizes less than 50 such as, for example, 46 can be desirable based on a balancing test between consumer expectations of having the capability of receiving accurate warnings about their glycemic state without having to do an excessive number of glucose measurements, and having a sufficiently number of glucose measurements to ensure a relative low number of false positive and false negative results.

After analyzing the plurality of glucose concentration measurements using the pattern recognition rules of hypoglycemic pattern 100, the pattern recognition rules of hyperglycemic pattern 200 may be performed. Thus, after performing the incidence of hypoglycemia by meal sub-routine 140, the method moves to the incidence of hyperglycemia sub-routine 210. If the percentage of hyperglycemic incidence Ph is greater than a pre-determined threshold, then the method moves to step 211 to determine whether the percentage of hyperglycemic incidence Ph equals about 100%. If the percentage of hyperglycemic incidence Ph is less than a pre-determined threshold, then the method moves to the incidence of hyperglycemia by meal sub-routine 240. The pre-determined threshold for the incidence of hyperglycemia sub-routine 210 may range from about 15% to about 50%.

For step 211, if the hyperglycemic frequency Ph equals about 100%, then the method moves to the frequency of glucose testing sub-routine 410. However, if the hyperglycemic frequency Ph does not equal about 100%, then the method moves to step 212 to determine whether more than about 27 glucose concentration measurements have been collected.

For step 212, if there are more than about 27 measurements, then the method moves to the hyperglycemic pattern by time slot sub-routine 220. However, if there are not more than about 27 measurements, then the method moves to the incidence of hyperglycemia by meal sub-routine 240. The sample size of 27 represents approximately the minimum number of glucose measurements required to perform sub-routine 120 and is based on several assumptions including: that a user tests at least once per day; that a user tests in at least two times; that there are at least two categories of observed incidences that are hyperglycemic incidences and not hyperglycemic incidences; and that the at least two categories each have greater than or equal to about five incidences. When using a chi-squared test, the minimum expected number of incidences is five for each category per time slot. Thus, two-time slots times two categories times five expected number of incidences gives approximately a minimum sample size of twenty. Based on the calculations, the sample size may be greater than about 20, and preferably be greater than about 27. For sample sizes greater than 20 such as, for example, 27 can be desirable based on a balancing test between consumer expectations of having the capability of receiving accurate warnings about their glycemic patterns without having to do an excessive number of glucose measurements, and having a sufficient number of glucose measurement to ensure a relative low number of false positive and false negative results.

The hyperglycemic pattern by time slot sub-routine 220 is performed if more than about 27 glucose concentration measurements were found in step 212. After performing the hyperglycemic pattern by time slot sub-routine 220, the method determines whether the plurality of glucose concentration measurements has more than about 46 measurements, as shown in step 228. If more than about 46 glucose concentration measurements have been collected, as shown in step 228, then the method moves to the hyperglycemic pattern by day of week sub-routine 230 and also to the incidence of hyperglycemia by meal sub-routine 240. If not more than about 46 glucose concentration measurements have been collected, as indicated in step 228, then the method moves to an incidence of hyperglycemia by meal sub-routine 240. The sample size of 46 measurements is based on several assumptions including: that a user tests at least once per day; that the user tests in at least five of the seven days per week; that there are at least two categories of observed incidences that are hyperglycemic incidences and not hyperglycemic incidences; and that the at least two categories each have greater than or equal to about five incidences for the at least five days of the week. When using a chi-squared test, the minimum expected number of incidences is five for each category per day of the week. Thus, five days times two categories times five expected counts gives a minimum sample size of 50. Based on the calculations, the sample size may be greater than about 50, and preferably be greater than about 46. For sample sizes less than 50 such as, for example, 46 can be desirable based on a balancing test between consumer expectations of having the capability of receiving accurate warnings about their glycemic state without having to do an excessive number of glucose measurements, and having a sufficiently number of glucose measurements to ensure a relative low number of false positive and false negative results.

After analyzing the plurality of glucose concentration measurements using the pattern recognition rules of hyperglycemic pattern 200, the pattern recognition rules of variability pattern 300 may be performed. That is, after performing the incidence of hyperglycemia by meal sub-routine 240, the method moves to step 301 to determine whether more than about 14 glucose concentration measurements have been collected. If more than about 14 glucose concentration measurements have been collected, then the method moves to the glucose variability range sub-routine 310, the overcorrection for hypoglycemia sub-routine 320, and to the overcorrection for hyperglycemia sub-routine 330. If not more than about 14 glucose concentration measurements have been collected, then the method moves to the overcorrection for hypoglycemia sub-routine 320 and also to the overcorrection for hyperglycemia sub-routine 330. A sample size of 14 or greater may be selected to ensure the presence of a clinically significant pattern. Based on statistics, a sample size of 4 is sufficient to determine statistically significant difference, but a larger sample size was selected as a conservative measure to increase the likelihood of identifying a clinically significant pattern.

In addition to the methodologies described above, variability in blood glucose can be correlated, as will be described further herein, to a specific time period during a day, a plurality of time periods in a day, a specified day of a week, a plurality of specified days in a week, glucose testing frequency having pre-meal tests in a specific time period during a day, frequency of glucose measurements (i.e., testing) for pre-meal test for specified days of the week, glucose testing frequency having post-meal tests in a specific period during a day, frequency of glucose measurements (i.e., testing) for post-meal test for specified days of the week.

The pattern recognition rule of testing dosing pattern 400 may be performed after one of two condition are met, which are 1) the completion of the overcorrection for hyperglycemia sub-routine 330 or 2) the percentage of hyperglycemic incidence Ph or the percentage of hypoglycemic incidence Pl equals about 100%, as illustrated in step 211 and step 111, respectively. If one of the two aforementioned conditions are met, then the method will then perform the following processes or sub-routines such as, for example, the frequency of glucose testing sub-routine 410, the adequacy of pre-meal testing sub-routine 420, and the adequacy of post-meal testing sub-routine 430.

After completing the pattern recognition rule of testing dosing pattern 400, the pattern recognition rules of comparative pattern 500 will be performed. As a first step in comparative pattern 500, the method will determine whether the number of blood glucose concentration measurements with a pre-meal flag A and the number of blood glucose concentration measurements with a post-meal flag B are both greater than about nine, as illustrated in step 501.

If both the number of blood glucose concentration measurements with a pre-meal flag A and the number of blood glucose concentration measurements with a post-meal flag B have more than about 9 flagged measurements, then the method will perform the comparison of pre-meal and post-meal glucose concentrations sub-routine 510, the comparison of daytime and nighttime glucose concentrations sub-routine 520, the comparison of previous and current hypoglycemic glucose incidence sub-routine 530, and the comparison of previous and current hyperglycemic incidence sub-routine 540. A sample size of 9 or greater may be selected to ensure the presence of a clinically significant pattern. Based on statistics, a sample size of 4 is sufficient to determine statistically significant difference, but a larger sample size was selected as a conservative measure to increase the likelihood of identifying a clinically significant pattern.

If either the number of blood glucose concentration measurements with a pre-meal flag A or the number of blood glucose concentration measurements with a post-meal flag B have less than about 9 flagged measurements, as illustrated in step 501, then the method will perform the comparison of daytime and nighttime glucose concentrations sub-routine 520, the comparison of previous and current hypoglycemic glucose incidence sub-routine 530, and the comparison of previous and current hyperglycemic incidence sub-routine 540.

The method may be completed after performing the comparison of previous and current hyperglycemic incidence sub-routine 540. The following will describe a more detailed description of the aforementioned processes or sub-routines (110, 120, 130, 140, 210, 220, 230, 240, 310, 320, 330, 410, 420, 430, 510, 520, 530, and 540).

Figures 4A, 4B:
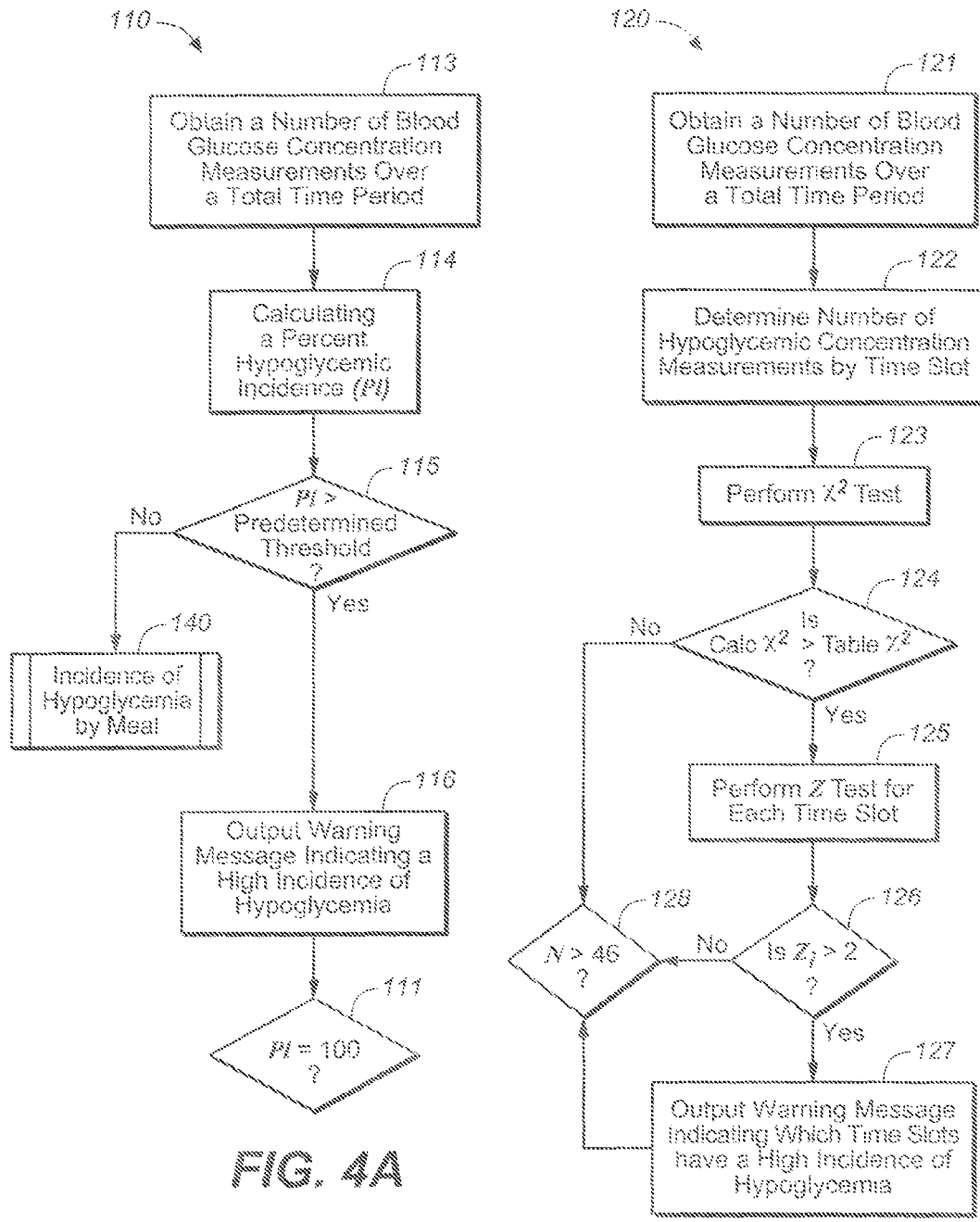
FIG. 4A illustrates a flow chart for analyzing a plurality of glucose concentration measurements for a pattern that may indicate an incidence of hypoglycemia.
FIG. 4B illustrates a flow chart for analyzing a plurality of glucose concentration measurements for a pattern that may indicate a hypoglycemic pattern by time slot.

FIG. 4A shows a flow chart of the incidence of hypoglycemia sub-routine 110, which may include obtaining a number of blood glucose concentration measurements over a total time period, as shown in step 113. Next, the sub-routine 110 may calculate a percentage of hypoglycemic incidence Pl for a total time period by summing a number of substantially hypoglycemic blood glucose concentration measurements divided by a number of blood glucose concentration measurements collected over the total time period, as shown in step 114. The total time period can be arbitrarily selected time duration such as, for example, hours in a day, a day, a week, a month, three months, six months, or between visits to a physicians or therapeutic regimens. Equation 1 shows an example of how to calculate percentage of hypoglycemic incidence Pl $$Pl = \frac{\sum_{i=1}^{n} L_i}{\sum_{i=1}^{n} N_i} *100 \qquad \text{Eq. 1}$$

In Equation 1, the term i represents a particular recurring time interval; n is a total number of recurring time intervals; and $L_i$ is a number of substantially hypoglycemic glucose concentration measurements that occur during time interval i; and $N_i$ represents the total number of glucose concentration measurements performed during time intervals i. The term $$\sum_{i=1}^{n} L_i$$

represents the total number of substantially hypoglycemic glucose concentration measurements for all of the recurring time intervals i. The term $$\sum_{i=1}^{n} N_i$$

represents the number of all glucose concentration measurements for all of the recurring time intervals i.

In step 115, the percentage of hypoglycemic incidence Pl may be compared to a predetermined threshold. A message may be displayed indicating a high incidence of hypoglycemia if the percentage of hypoglycemic incidence Pl is greater than a pre-determined threshold, as shown in step 116. If the percentage of hypoglycemic incidence Pl is not greater than a pre-determined threshold, then the sub-routine 110 may move to the incidence of hypoglycemia by meal sub-routine 140. In one embodiment, the pre-determined threshold may range from about 3% to about 15%. In the preferred embodiment, the threshold is about 5%. Alternatively, the threshold may be of any value as selected by a clinician or physician. After displaying a warning message in step 116, the sub-routine may move to step 111.

In particular, a hypoglycemic pattern by time slot sub-routine 120 may be used to determine if there is a high incidence of hypoglycemia occurring at a particular recurring time interval i. In one embodiment, the time interval may recur daily and be equal to about one eighth of a day. The eight daily time slots may include before breakfast, after breakfast, before lunch, after lunch, before dinner, after dinner, bedtime, and overnight, which can be pre-defined by default management settings or customized by the user. Note that a recurring time interval may also be referred to as a time slot.

FIG. 4B shows a flow chart of the hypoglycemic pattern by time slot sub-routine 120 that may include obtaining a number of blood glucose measurements over a total time period in step 121 and determining a number of hypoglycemic incidences for each of the time slots in step 122. Next, the sub-routine 120 determines whether the number of hypoglycemic incidence for at least one of the time slots is different using a statistical test such as, for example, a chi-squared test (as shown in a template of FIG. 4C), and as shown in step 123. In step 124, the calculated chi-squared value is compared to a chi-squared value in a suitable table, shown here as a template in FIG. 4C for a chi-squared table. It should be noted that, for brevity in the disclosure, the nomenclatures of this table in FIG. 4C are the same nomenclatures provided in the forthcoming statistical analysis technique.

Referring back to FIG. 4, if the calculated chi-squared is not greater than a chi-squared value in a table (of which a template is shown in FIG. 4C), then the sub-routine 120 moves to step 128. If the calculated chi-squared is greater than the chi-squared value in a table (of which a template is shown in FIG. 4C), then the sub-routine 120 moves to perform a Z test for each time slot, as shown in step 125. In one embodiment, the Z test may be a two-sided Z test. In step 126, the calculated $Z_i$ value is compared to a value of about 2. If the calculated $Z_i$ is greater than about 2, then a message indicating a high incidence of hypoglycemia has occurred at a particular time slot will be displayed, as shown in step 127. After displaying the message, the subroutine 120 moves to the step 128. If the calculated $Z_i$ is not greater than about 2, then the sub-routine 120 moves to the step 128.

In one embodiment, a chi-squared test may be used to determine if any of the time slots are statistically significantly different from each other. The chi-squared test may use a confidence level ranging from about 95% to about 99%. Equation 2 shows an example of how to calculate chi-squared $\chi^2$.

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}} \qquad \text{Eq. 2}$$

In Equation 2, the term $L'_i$ is a number of non-hypoglycemic glucose concentration measurements that occur during time interval i. $L_{i,pre}$ is a predicted number of substantially hypoglycemic glucose concentration measurements that will occur during time interval i. $L'_{i,pre}$ is a predicted number of non-hypoglycemic glucose concentration measurements that will occur during time interval i. After determining $\chi^2$ using Equation 2, the calculated $\chi^2$ value is compared to a $\chi^2$ in a table based on a number of degrees of freedom for each of the time intervals i. If the calculated $\chi^2$ is greater than the $\chi^2$ value on the table, then at least one of the time intervals is statistically significantly different.

The term $L_{i,pre}$ may be calculated using Equation 3a.

$$L_{i,pre} = \frac{\sum_{i=1}^{n} L_i}{\sum_{i=1}^{n} N_i} * N_i \qquad \text{Eq. 3a}$$

The term $L'_{i,pre}$ may be calculated using Equation 3b.

$$L'_{i,pre} = \frac{\sum_{i=1}^{n} L'_i}{\sum_{i=1}^{n} N_i} * N_i \qquad \text{Eq. 3b}$$

The term $$\frac{\sum_{i=1}^{n} L_i}{\sum_{i=1}^{n} N_i}$$

represents a fraction that estimates the likelihood of observing a hypoglycemic event based on all of the recurring time intervals combined.

The method of performing the hypoglycemic pattern by time slot sub-routine 120 may further include identifying which one of the recurring time intervals i is statistically significantly different using a Z test if the chi-squared test determines that at least one of the time intervals is statistically significantly different. Equation 4 shows an example of the Z test.

$$Z_i = \frac{(L_i - L_{i,pre})}{SE_i} \qquad \text{Eq. 4}$$

The term $Z_i$ represents a Z value at a particular time interval i and $SE_i$ represents a standard error for a particular time interval i. The term $SE_i$ may be calculated using Equation 5.

$$SE_i = \sqrt{\frac{1}{N_i} * L_{i,pre} * (N_i - L_{i,pre})} \qquad \text{Eq. 5}$$

A $Z_i$ value may be calculated for each recurring time interval i and compared to a Z value in a table. If the $Z_i$ value for one of the recurring time intervals is greater than the Z value in the table (e.g., about two), then the particular recurring time interval i is statistically significantly different.

The hypoglycemic pattern by day of the week sub-routine 130 may be performed in a manner similar to hypoglycemic pattern by time slot sub-routine 120. In the hypoglycemic pattern by day of the week sub-routine 130, the time intervals recur weekly where there are seven time slots to represent each day of the week.

FIG. 5 shows a flow chart of the hypoglycemic pattern by day of week 130 that may include obtaining a number of blood glucose measurements over a total time period in step 131 and determining a number of hypoglycemic incidences for each day in step 132. Next, the sub-routine 130 determines whether the number of hypoglycemic incidence for at least one of the days is different using a statistical test such as, for example, a chi-squared test (as shown in a template of FIG. 4C), and as shown in step 133. The calculated chi-squared value is compared to a chi-squared value in a table, as shown in step 134. If the calculated chi-squared is not greater than a chi-squared value in a table (of which a template is shown in FIG. 4C), then the sub-routine 130 moves to the next sub-routine 140. If the calculated chi-squared is greater than the chi-squared value in a table (of which a template is shown in FIG. 4C), then the sub-routine 130 moves to perform a Z test for each day of the week, as shown in step 135. In step 136, the calculated $Z_i$ value is compared to a value of about 2. If the calculated $Z_i$ is greater than about 2, then a message indicating a high incidence of hypoglycemia has occurred at a particular day of the week will be displayed, as shown in step 137. After displaying the message, the subroutine 130 moves to the next sub-routine 140. If the calculated $Z_i$ is not greater than about 2, then the sub-routine 120 moves to the next sub-routine 140.

FIG. 6 shows a flow chart of the hypoglycemia by meal sub-routine 140 that may be used to determine if there is a high incidence of hypoglycemia occurring at either a pre-meal or post-meal time interval. The incidence of hypoglycemia by meal sub-routine 140 may include obtaining a number of blood glucose concentration measurements over a total time period, as shown in step 141. A number of blood glucose concentration measurements with a pre-meal tag A and post-meal tag B may be calculated indicating the number of blood glucose measurement performed before eating a meal and after a meal, respectively, as shown in step 142. A number of substantially hypoglycemic blood glucose concentration measurements with a pre-meal tag $L_A$ and post-meal tag $L_B$ may be calculated, as shown in step 143. The percentage of hypoglycemic incidence having a pre-meal tag $Pl_A$ and a post-meal tag $Pl_B$ may be calculated, as indicated in step 144. $Pl_A$ may be determined by dividing the number of substantially hypoglycemic blood glucose concentration measurements that have the pre-meal flag $L_A$ by the number of blood glucose concentration measurements with the pre-meal tag A. Similarly, $Pl_B$ may be determined by dividing the number of substantially hypoglycemic blood glucose concentration measurements that have the pre-meal flag $L_B$ by the number of blood glucose concentration measurements with a pre-meal B.

Equations 6 and 7 illustrate a mathematical embodiment on how to determine the percentage of hypoglycemic incidence having a pre-meal tag $Pl_A$ and a post-meal tag $Pl_B$.

$$Pl_A = \frac{L_A}{A} * 100 \qquad \text{Eq. 6}$$

$$Pl_B = \frac{L_B}{B} * 100 \qquad \text{Eq. 7}$$

The percentage of hypoglycemic incidence having a pre-meal tag $Pl_A$ and a post-meal tag $Pl_B$ may be compared to a pre-determined threshold, as shown in step 145. If either $Pl_A$ or $Pl_B$ is greater than a pre-determined threshold, then a message can be displayed indicating a high incidence of hypoglycemia occurring at a pre-meal time and/or a post-meal time, as shown in step 146. If $Pl_A$ and $Pl_B$ are not greater than a pre-determined threshold, then sub-routine 140 may move to the incidence of hyperglycemia sub-routine 210. After displaying a message in step 146, the sub-routine 140 may move to the incidence of hyperglycemia sub-routine 210. In one embodiment, the pre-determined threshold may range from about 10% to about 25%.

Figures 7A, 7B:
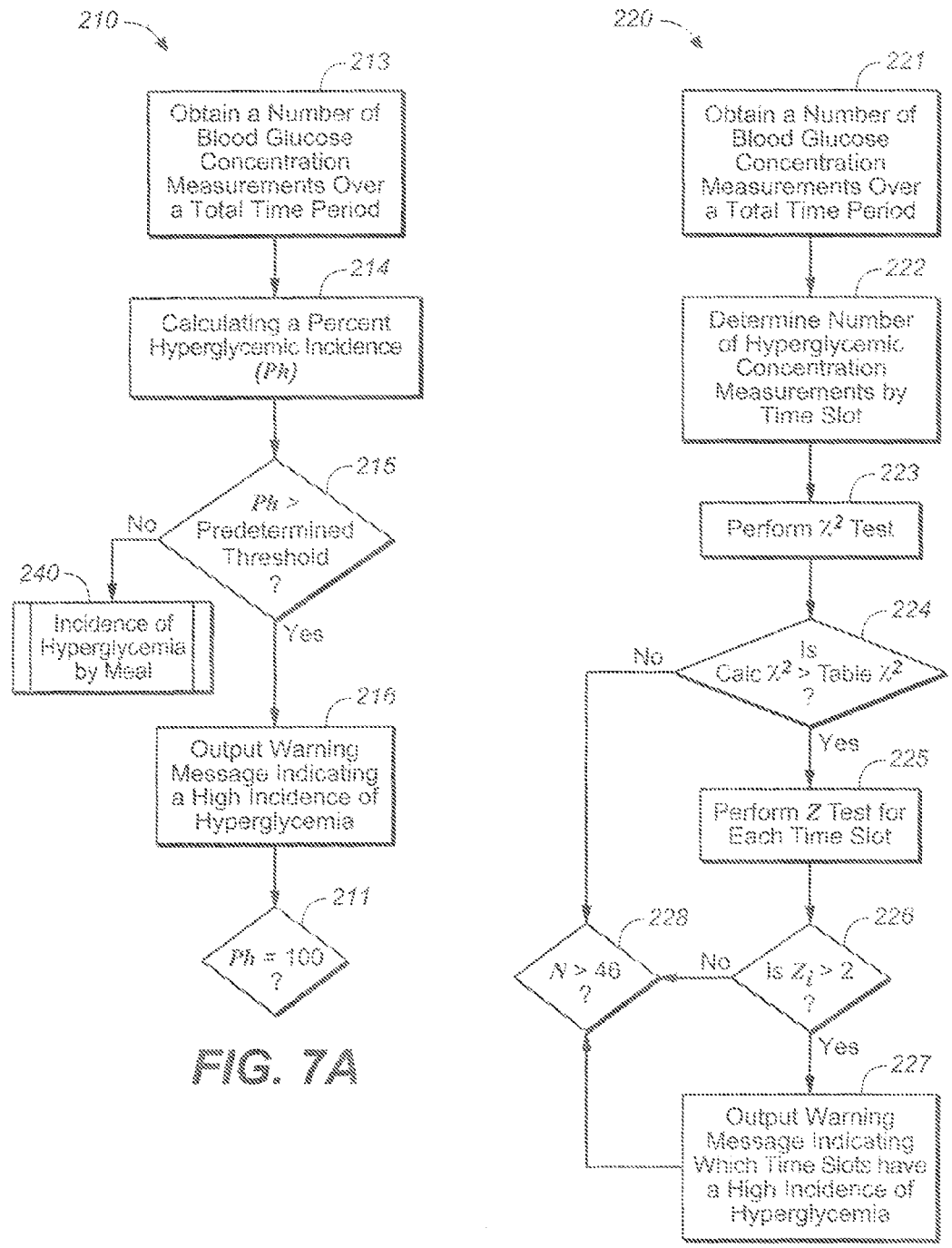
FIG. 7A illustrates a flow chart for analyzing a plurality of glucose concentration measurements for a pattern that may indicate an incidence of hyperglycemia.
FIG. 7B illustrates a flow chart for analyzing a plurality of glucose concentration measurements for a pattern that may indicate a hyperglycemic pattern by time slot.

FIG. 7A shows a flow chart of the incidence of hyperglycemia sub-routine 210, which may include obtaining a number of blood glucose concentration measurements over a total time period, as shown in step 213. The total time period can be any arbitrarily selected time duration, such as, for example, number of hours in a day, one day, one week, one month, three months, six months, time between visits to a physician's office, and so on. Next, the sub-routine 210, as implemented in a suitable computer, may calculate a percentage of hyperglycemic incidence Ph for a total time period by summing a number of substantially hyperglycemic blood glucose concentration measurements divided by a number of blood glucose concentration measurements collected over the total time period, as shown in step 214. Equation 8 shows an example of how to calculate percentage of hyperglycemic incidence Ph $$Ph = \frac{\sum_{i=1}^{n} H_i}{\sum_{i=1}^{n} N_i} * 100 \qquad \text{Eq. 8}$$

The term i represents a particular recurring time interval; n is a total number of recurring time intervals; and $H_i$ is a number of substantially hyperglycemic glucose concentration measurements that occur during time interval i; and $N_i$ represents the total number of glucose concentration measurements performed during time intervals i. The term $$\sum_{i=1}^{n} H_i$$

represents the total number of substantially hyperglycemic glucose concentration measurements for all of the recurring time intervals i. The term $$\sum_{i=1}^{n} N_i$$

represents the number of all glucose concentration measurements for all of the recurring time intervals i.

In step 215, the percentage of hyperglycemic incidence Ph may be compared to a predetermined threshold. A message may be displayed indicating a high incidence of hyperglycemia if the percentage of hyperglycemic incidence Ph is greater than a pre-determined threshold, as shown in step 216. If the percentage of hyperglycemic incidence Ph is not greater than a pre-determined threshold, then the sub-routine 110 may move to the incidence of hyperglycemia by meal sub-routine 240. In one embodiment, the pre-determined threshold may range from about 15% to about 50%. After displaying a warning message in step 216, the sub-routine may move to step 211.

The hyperglycemic pattern by time slot sub-routine 220 may be used to determine if there is a high incidence of hyperglycemia occurring at a particular recurring time interval i. FIG. 7A shows a flow chart of the hyperglycemic pattern by time slot sub-routine 220 that may include obtaining a number of blood glucose measurements over a total time period in step 221 and determining a number of hyperglycemic incidences for each of the time slots in step 222. Next, the sub-routine 220 determines whether the number of hyperglycemic incidence for at least one of the time slots is different using a statistical test such as, for example, a chi-squared test (as shown in a template of FIG. 4C), and as shown in step 223. The calculated chi-squared value is compared to a chi-squared value in a table, as shown in step 224. If the calculated chi-squared is not greater than a chi-squared value in a table (of which a template is shown in FIG. 4C), then the sub-routine 220 moves to step 228. If the calculated chi-squared is greater than the chi-squared value in a table (of which a template is shown in FIG. 4C), then the sub-routine 220 moves to perform a Z test for each time slot, as shown in step 225. In one embodiment, the Z test may be a two-sided Z test. In step 226, the calculated $Z_i$ value is compared to a value of about 2. If the calculated $Z_i$ is greater than about 2, then a message indicating a high incidence of hyperglycemia has occurred at a particular time slot will be displayed, as shown in step 227. After displaying the message, the subroutine 220 moves to the step 228. If the calculated $Z_i$ is not greater than about 2, then the sub-routine 220 moves to the step 228.

In one embodiment, a chi-squared test may be used to determine if any of the time slots are statistically significantly different. The chi-squared test may use a confidence level ranging from about 95% to about 99%. Equation 9 shows an example of how to calculate chi-squared $\chi^2$.

$$\chi^2 = \sum_{i=1}^{n} \frac{(H_i - H_{i,pre})^2}{H_{i,pre}} + \sum_{i=1}^{n} \frac{(H'_i - H'_{i,pre})^2}{H'_{i,pre}} \qquad \text{Eq. 9}$$

In Equation 9, the term $H'_i$ is a number of non-hyperglycemic glucose concentration measurements that occur during time interval i. $H_{i,pre}$ is a predicted number of substantially hyperglycemic glucose concentration measurements that will occur during time interval i. $H'_{i,pre}$ is a predicted number of non-hyperglycemic glucose concentration measurements that will occur during time interval i. After determining $\chi^2$ using Equation 9, the calculated $\chi^2$ value is compared to a $\chi^2$ in a table based on a number of degrees of freedom for each of the time intervals i. If the calculated $\chi^2$ is greater than the $\chi^2$ value on the table, then at least one of the time intervals is statistically significantly different.

The term $H_{i,pre}$ may be calculated using Equation 10a.

$$H_{i,pre} = \frac{\sum_{i=1}^{n} H_i}{\sum_{i=1}^{n} N_i} * N_i \qquad \text{Eq. 10a}$$

The term $H'_{i,pre}$ may be calculated using Equation 10b.

$$H'_{i,pre} = \frac{\sum_{i=1}^{n} H'_i}{\sum_{i=1}^{n} N_i} * N_i \qquad \text{Eq. 10b}$$

The term $$\frac{\sum_{i=1}^{n} H_i}{\sum_{i=1}^{n} N_i}$$

represents a fraction that estimates the likelihood of observing a hyperglycemic event based on all of the recurring time intervals combined.

The method of performing the hyperglycemic pattern by time slot sub-routine 220 in FIG. 7B may further include identifying which one of the recurring time intervals i is statistically significantly different using a Z test if the chi-squared test determines that at least one of the time intervals is statistically significantly different. Equation 11 shows an example of the Z test.

$$Z_i = \frac{(H_i - H_{i,pre})}{SE_i} \qquad \text{Eq. 11}$$

In Equation 11, the term $Z_i$ represents a Z value at a particular time interval i and $SE_i$ represents a standard error for a particular time interval i. The term $SE_i$ may be calculated using Equation 12.

$$SE_i = \sqrt{\frac{1}{N_i} * H_{i,pre} * (N_i - H_{i,pre})} \qquad \text{Eq. 12}$$

A $Z_i$ value may be calculated for each recurring time interval i and compared to a Z value in a table. If the $Z_i$ value for one of the recurring time intervals is greater than the Z value in the table (e.g., about two), then the particular recurring time interval i is statistically significantly different.

The hyperglycemic pattern by day of the week sub-routine 230 may be performed in a manner similar to hyperglycemic pattern by time slot sub-routine 220. In the hyperglycemic pattern by day of the week sub-routine 230, the time intervals recur weekly where there are seven time slots to represent each day of the week.

FIG. 8 shows a flow chart of the hyperglycemic pattern by day of week 230 that may include obtaining a number of blood glucose measurements over a total time period in step 231 and determining a number of hyperglycemic incidences for each day in step 232. Next, the sub-routine 230, as implemented on a suitable computing device, determines whether the number of hyperglycemic incidence for at least one of the days is different using a statistical test such as, for example, a chi-squared test (as shown in a template of FIG. 4C), and as shown in step 233. The calculated chi-squared value is compared to a chi-squared value in a table, as shown in step 234. If the calculated, chi-squared is not greater than a chi-squared value in a table (of which a template is shown in FIG. 4C), then the sub-routine 230 moves to the next sub-routine 240. If the calculated chi-squared is greater than the chi-squared value in a table (of which a template is shown in FIG. 4C), then the sub-routine 230 moves to perform a Z test for each day of the week, as shown in step 235. In step 236, the calculated $Z_i$ value is compared to a value of about 2. If the calculated $Z_i$ is greater than about 2, then a message indicating a high incidence of hyperglycemia has occurred at a particular day of the week will be displayed, as shown in step 237. After displaying the message, the subroutine 230 moves to the next sub-routine 240. If the calculated $Z_i$ is not greater than about 2, then the sub-routine 220 moves to the next sub-routine 240.

FIG. 9 shows a flow chart of the hyperglycemia by meal sub-routine 240 that may be used to determine if there is a high incidence of hyperglycemia occurring at either a pre-meal or post-meal time interval. The incidence of hyperglycemia by meal sub-routine 240 may include obtaining a number of blood glucose concentration measurements over a total time period, as shown in step 241. A number of blood glucose concentration measurements with a pre-meal tag A and post-meal tag B may be calculated indicating the number of blood glucose measurement performed before eating a meal and after a meal, respectively, as shown in step 242. A number of substantially hyperglycemic blood glucose concentration measurements with a pre-meal tag $H_A$ and post-meal tag $H_B$ may be calculated, as shown in step 243. The percentage of hyperglycemic incidence having a pre-meal tag $Ph_A$ and a post-meal tag $Ph_B$ may be calculated, as indicated in step 244. $Ph_A$ may be determined by dividing the number of substantially hyperglycemic blood glucose concentration measurements that have the pre-meal flag $H_A$ by the number of blood glucose concentration measurements with the pre-meal tag A. Similarly, $Ph_B$ may be determined by dividing the number of substantially hyperglycemic blood glucose concentration measurements that have the pre-meal flag $H_B$ by the number of blood glucose concentration measurements with a pre-meal tag B.

Equations 13 and 14 illustrate a mathematical embodiment on how to determine the percentage of hyperglycemic incidence having a pre-meal tag $Ph_A$ and a post-meal tag $Ph_B$.

$$Ph_A = \frac{H_A}{A} * 100 \quad \text{Eq. 13}$$

$$Ph_B = \frac{H_B}{B} * 100 \quad \text{Eq. 14}$$

The percentage of hyperglycemic incidence having a pre-meal tag $Ph_A$ and a post-meal tag $Ph_B$ may be compared to a pre-determined threshold, as shown in step 245. If either $Ph_A$ or $PH_B$ is greater than a pre-determined threshold, then a message can be displayed indicating a high incidence of hyperglycemia occurring at a pre-meal time and/or a post-meal time, as shown in step 246. If $Ph_A$ and $Ph_B$ are not greater than a pre-determined threshold, then sub-routine 240 may move to step 301, which is a first step in variability pattern rules 300. After displaying the message in step 246, the sub-routine 240 may move to the step 301. In one embodiment, the pre-determined threshold may range from about 15% to about 50%.

Referring to FIGS. 4-8, a method is provided that includes storing a patient's data that includes blood glucose concentration measurements; generating from the patient's data a suitable table having predetermined conditions (e.g., Time or Day) and outcomes (e.g., Hypoglycemic, Hyperglycemic or Other condition) upon indication of instances of hypoglycemia, hyperglycemia, or excessive blood glucose variability by time of day, by day in a week, both by time of day and day of week, or at different time intervals; calculating standard error (SE) and Z test with data from the table; and displaying a message when the Z test being greater than a predetermined value indicative of a pattern of glycemia outside at least a predetermined range for such pattern. In the preferred embodiment, a threshold for the Z test is about 2.

The glucose variability range sub-routine 310 may be used to indicate to a user if their glucose concentration has a wide range of blood glucose variability, as illustrated in FIG. 10. The glucose variability range sub-routine 310 may include obtaining a number of blood glucose measurements over a total time period in step 311, and ranking all of the blood glucose measurements based on a magnitude of the blood glucose measurement in step 312. Next, an inter quartile range may be determined that includes an upper ranking and a lower ranking in step 313. The upper ranking may correlate to an upper glucose concentration and the lower ranking may correlate to a lower glucose concentration. The inter quartile range selected here can be a glucose measurement in the $75^{th}$ and $25^{th}$ percentile. However, other suitable ranges can also be utilized, such as, for example, $80^{th}$ and $20^{th}$ percentiles or $90^{th}$ and $10^{th}$ percentiles. In step 314, the upper glucose concentration is subtracted from the lower glucose concentration to calculate a differential value or, for example, an inter quartile range. If the differential value is greater than a pre-determined threshold, a message may be displayed indicating an incidence of high blood glucose variability as shown in step 315. If the differential value is not greater than a pre-determined threshold, the sub-routine 310 may move to the over-correction for hypoglycemia sub-routine 320. After displaying the message in step 315, the sub-routine 310 may move to the overcorrection for hypoglycemia sub-routine 320. In one embodiment, the message is displayed only if there is a statistically significant number of blood glucose measurements collected by the glucose meter such as, for example, about greater than about fourteen blood glucose measurements, as shown in step 301 in FIG. 3A. An example of the pre-determined threshold for the glucose variability range sub-routine 310 may range from about 30 mg/dL to about 90 mg/dL, and preferably about 50 mg/dL.

Variability can also be associated graphically with incidences of hypoglycemia or hyperglycemia at a specified time of day or in association with a meal slot. Other associations of blood glucose variability can be with a specified date, day of week, timing of meals or insulin injections. Specifically, the system performs a generating of blood glucose variability pattern by determining (a) a median of glucose concentration values during a temporal period and (b) a median of test times during the temporal period; and correlating (a) the median of glucose concentration values and (b) the median of test times to define a data point on a two-dimensional coordinate graph having glucose values and test times. A suitable range (e.g., interquartile, $10^{th}$ and $90^{th}$ percentiles or $20^{th}$ and $80^{th}$ percentiles) can be plotted around each median data point. As shown in an example in FIG. 18, the temporal time period is selected to be a time period TP from 3:00 AM to 8:00 AM where a median of glucose concentration values is indicated by MGV of approximately 325 mg/dL during this time period with a median of the number of test measurements MT being approximately 4:00 AM, and both MGV and MT can be utilized to define a median data point on a two-dimensional chart for glucose value and time in display area D4. Association of blood glucose variability for MGV and MT can be determined for other specified indicators such as, for example, pre or post meal glucose concentration levels by time slot in a day or by days in a week or month, hypoglycemia, hyperglycemia, day of week, dates of week, or any time related specified indicator as deemed suitable by the user, patient, physician, or clinician. Thereafter, a suitable variability indicator (such as, for example, the interquartile range defined as a difference between the $75^{th}$ and $25^{th}$ percentile) can be determined around each of the median data. In the example illustrated in FIG. 18, the data values defining the $75^{th}$ percentile can be connected together as smoothed curve 700 about the median values defining curve 710 with the $25^{th}$ percentile values defining curve 720. The curves 700 and 720 serve to show graphically the blood glucose variability around the median value associated with a specified indicator (e.g., glucose, insulin, or other physiological indicators).

In the preferred embodiments, the median is a preferred indicator of a tendency in the blood glucose data to centralize about some value, i.e., a central tendency. The median is also preferred over other indicator such as, for example, the arithmetic mean because it has been observed that measurement data from blood glucose meter do not follow a normal or Gaussian distribution (i.e., an asymmetric instead of symmetric distribution), as it would be for other indicators. Further, the use of the median is preferred because (a) the median is insensitive to outlier data, and (b) the median is essentially unaffected by values outside a range of measurement of blood glucose meters. It is believed values for the median are highly correlated to the mean, and that correlation between median blood glucose level and HbA1c values would be very close to the mean blood glucose and HbA1c. However, for precision, it is believed that more sampling data would be required the median as compared to the mean.

Referring back to FIG. 18, the respective curves 700, 710, and 720 can be generated by a suitable interpolation technique, i.e., "curve smoothing," such as, for example, polynominal interpolation, cubic-Bezier spline, cubic cardinal spline, Fritsch-Carlson monotony preserving cubic interpolation, Akima cubic spline interpolation, rational cubic spline, or exponential interpolation. In the preferred embodiments, the curve smoothing is generated via a cardinal spline through a specified array of point structures using a tension of 1.

Heretofore, a method of assessing glycemia of a patient can be provided to provide a graphical comparison of insulin intake and blood glucose along with any other physiological parameters. The method can be achieved by collecting data related to a patient glycemia, including blood glucose measurements and insulin intake values; determining a combined median of glucose and time as a function of a median of blood glucose values and a median of time periods for each measurement of the blood glucose values over a predetermined temporal period; and displaying the combined median of glucose and time in a graphical format. The collecting can include collecting data of the patient over a plurality of temporal time periods. The determining can include determining the combined median of glucose and time for each of the plurality of temporal time periods. In particular, the displaying can include generating a graphical chart for each of the determining and establishing, where the charts have substantially the same temporal time periods.

Once the combined median of glucose and time has been determined, blood glucose variability can be generated by a suitable technique, such as, for example, using the inter quartile range. To show trends or patterns, the blood glucose variability can be obtained for each combined median of glucose and time over the plurality of temporal periods. And as used herein, the temporal periods can be any unit indicator of time such as for example, every 4 hours, every 8 hours, every 24 hours, day or days in a week, specific dates, every week or every month and so on.

The system can be utilized to associate the variability of glucose concentration with the intake of insulin via a common specified indicator (e.g., time of day, day of week, and others) to assess the effects of insulin, types of insulin, or frequency of insulin intake. Specifically, the system performs a generating of blood glucose variability pattern by determining (based on a common indicator of temporal time TP) the following: (i) a median of insulin doses MI taken by the patient during the temporal period selected above and (ii) a median of dosage times MIT during the temporal period and it would correlate both (i) the median of insulin doses MI and (ii) the median of the number of insulin intake values MIT to define a data point on a two-dimensional coordinate graph having insulin doses and dosage times as its ordinate and abscissa, respectively. In particular, the method above can be implemented to establish a combined median of insulin intake and time as a function of both (i) median of insulin intake and (ii) a median of time periods for each insulin intake over the predetermined temporal period; and displaying the combined median of insulin intake and time in a graphical format so that a clinician, patient or diabetes specialist would be able to assess generally the effect of insulin intake and blood glucose. This correlation of the median insulin doses and dosage time can be plotted graphically in an exemplary two-dimensional chart within display area D5, which then can be utilized to show the association in the variability of glucose in the chart of display area D4 and insulin in the chart of display area D5 by the common specified indicator of "time of day." It should be noted that the chart in display area D4 or D5 is not limited to a two-dimensional chart but that other types of charts can be utilized such as, for example, three-dimensional charts or charts using graphical representation for more than 4 different variable data inputs.

Although blood glucose variability has been described generally in relation to the median and interquartile range of blood glucose values, other techniques can be utilized, such as, for example:

"standard deviation" or SD,

"coefficient of variation" CV,

"average-daily-blood-glucose",

"N70+N180" where the number of blood glucose below 70 mg/dL and the number above 180 mg/dL are utilized, "M value" derived as a composite measure of glycemic control from blood glucose data, as described by J. Schlichtkrull et al., *The M-Value, an Index of Blood-Sugar Control in Diabetics*, Acta Medica Scandinavia, Vol. 177, fasc. 1, 1965, pp. 95-93, "mean-amplitude-of-glycemic-excursion," as discussed by F. John Service et al., in *Mean Amplitude of Glycemic Excursions, a Measure of Diabetic Instability*, Diabetes, Vol. 19, No. 9, pp. 644-655, September 1970, "lability index" as described by Kovatchev B P et al., in *Methods for Quantifying Self-monitoring Blood Glucose Profile Exemplified by an Examination of Blood Glucose Pattern in Patients with Type 1 and Type 2 Diabetes*, Diabetes Technology and Therapeutics, 4: 295-303, 2002, "absolute-blood-glucose-rate-of-change" for readings less than 4 hours apart as discussed by Ryan E A et al., in *Assessment of the Severity of Hypoglycemia and Glycemic Lability in Type 1 Diabetic Subjects Undergoing Islet Transplantation*, Diabetes 53: 955-962, 2004, "Figure of Merit," as described by Rodbard, D. (2005), *Improved Methods for Calculating a "Figure of Merit" for Blood Glucose Monitoring Data*, Diabetes Technology Meeting, San Francisco, Calif., November 2005, "J-index," as described by Wojcicki, J. (1995), *J-Index, A New Proposition Of The Assessment Of Current Glucose Control In Diabetic Patients*, Horm Metab Res., 27, 41-42, and "average-daily-risk-range" as described by Otto et al., in Diabetes Care, Vol. 29, No. 11, pp. 2433-2438 (November 2006).

Other documents relating to the potential hazards posed by variability in blood glucose values are described in Hirsch I B. *Glycemic Variability: It's Not Just About A1C Anymore!* Diabetes Technol Ther. 2005; 7:780-783; Brownlee M, Hirsch, L B. Glycemic variability: *A Hemoglobin A1c—Independent Risk Factor For Diabetic Complications*. JAMA 2006; 295 (14): 1707-1708; and Monnier L, Mas E, Ginet C, et al., *Activation Of Oxidative Stress By Acute Glucose Fluctuations Compared With Sustained Chronic Hyperglycemia In Patients With Type 2 Diabetes*. JAMA. 2006; 295:1681-1687. The above-cited documents are hereby incorporated by reference in their entireties into this application.

The overcorrection for hypoglycemia sub-routine 320, as illustrated in FIG. 11, may be used to determine if a user has ingested a bolus of carbohydrate that caused the user's blood glucose concentration to increase from a hypoglycemic state to a hyperglycemic state. Ideally, a user would want to ingest a bolus of carbohydrate to cause a switch from the hypoglycemic state to the euglycemic state.

The overcorrection for hypoglycemia sub-routine 320 may include obtaining a number of blood glucose measurements over a total time period as shown in step 321, and measuring a first blood glucose concentration that is less than a first pre-determined threshold, as shown in step 322. The first pre-determined threshold may be about 70 mg/dL where a blood glucose concentration that is less than the first predetermined threshold is hypoglycemic. The first blood glucose concentration indicates that the user is in a hypoglycemic state. In step 323, all blood glucose measurements performed from about 30 minutes to about 240 minutes after the first blood glucose concentration measurement are evaluated for hyperglycemia. If one of the blood glucose concentrations are found to be greater than about a second pre-determined threshold, then a message is displayed indicating a possible presence of overcorrection for hypoglycemia, as shown in step 324. The second pre-determined threshold may be about 180 mg/dL. If none of the blood glucose concentrations are found to be greater than about the second pre-determined threshold, then the subroutine 320 may move to the overcorrection for hypoglycemia sub-routine 330. After displaying the message in step 324, the sub-routine 320 may move to the overcorrection for hyperglycemia sub-routine 330.

The overcorrection for hyperglycemia sub-routine 330, as illustrated in FIG. 12, may be used to determine if a user has taken a bolus of insulin such that the user's glucose concentration decreased from a hyperglycemic state to a hypoglycemic state. Ideally, a user may want an insulin bolus to cause a switch from the hyperglycemic state to the euglycemic state.

The overcorrection for hyperglycemia sub-routine 330 may include obtaining a number of blood glucose measurements over a total time period as shown in step 331, and measuring a first blood glucose concentration that is greater than a second pre-determined threshold, as shown in step 332. The second pre-determined threshold may be about 180 mg/dL where a blood glucose concentration that is greater than the second pre-determined threshold is hyperglycemic. In step 333, all blood glucose measurements performed from about 30 minutes to about 240 minutes after the first blood glucose concentration measurement are evaluated for hypoglycemia. If one of the blood glucose concentrations are found to be less than about a first pre-determined threshold, then a message is displayed indicating a possible presence of overcorrection for hyperglycemia, as shown in step 334. The first pre-determined threshold may be about 70 mg/dL. If none of the blood glucose concentrations are found to be less than about the first pre-determined threshold, then the sub-routine 330 may move to the frequency of glucose testing sub-routine 410. After displaying the message in step 334, the sub-routine 330 may move to the frequency of blood glucose testing sub-routine 410.

FIG. 13 shows a flow chart for the frequency of blood glucose testing sub-routine 410, which may include obtaining a number of blood glucose measurements over a total time period, as shown in step 411. Next, an average number of blood glucose concentration measurements per day or per week may be calculated, as shown in step 412. In step 413, the average number of average number of blood glucose concentration measurements per unit time is compared to a pre-determined threshold. A message may be displayed indicating that the average number of blood glucose concentration measurements per unit time is not sufficient if the average number of blood glucose concentration measurements per unit time is less than a pre-determined threshold, as shown in step 414. If the average number of blood glucose concentration measurements per unit time is not less than a pre-determined threshold, the sub-routine 410 may move to the adequacy of pre-meal testing sub-routine 420. After displaying the message in step 414, the sub-routine 410 may move to the adequacy of pre-meal testing sub-routine 420. In one embodiment, the pre-determined threshold may range from about 3 measurements per week to about 15 measurements per week.

Figure 14A:
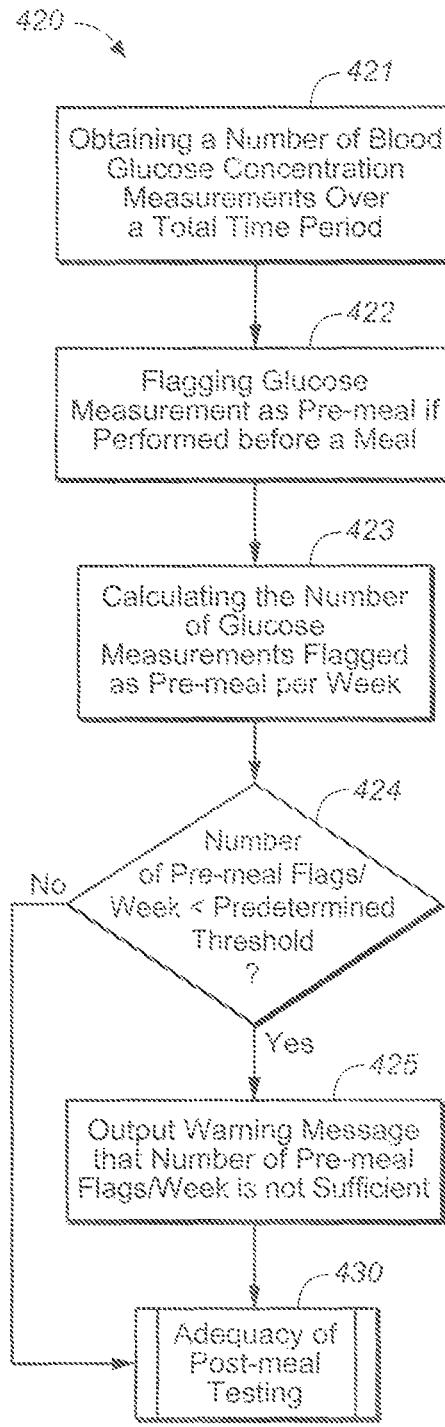
FIG. 14A illustrates a flow chart for analyzing a plurality of glucose concentration measurements for a pattern that may indicate whether the adequacy of pre-meal testing is sufficient.

FIG. 14A shows a flow chart for the adequacy of pre-meal testing sub-routine 420, which may include obtaining a number of blood glucose measurements over a total time period, as shown in step 421. Next, the blood glucose concentration measurement may be flagged as pre-meal if the blood glucose concentration measurement was performed before a meal, as shown in step 422. A number of blood glucose concentration measurements per week that are flagged as pre-meal can be determined, as shown in step 423. In step 424, the number of blood glucose concentration measurements flagged as pre-meal per week is compared to a pre-determined threshold. A warning message may be displayed if the number of blood glucose concentration measurements per week that are flagged as pre-meal is less than a pre-determined threshold, as shown in step 425. In one embodiment, the pre-determined threshold may range from about 3 pre-meal flags per week to about 7 pre-meal flags per week. However, it should be noted that the appropriate threshold is one that can be set by the physician or automatically or semi-automatically via a suitable algorithm by taking into account the average number of tests per day or per week, the pattern of testing being used, and the pattern of testing recommended by the physician. If the number of blood glucose concentration measurements per week that are flagged as pre-meal is not less than a pre-determined threshold, then the sub-routine 420 may move to the adequacy of post-meal testing sub-routine 430. After displaying the message in step 425, the sub-routine 420 may move to the adequacy of post-meal testing sub-routine 430. In other instances, where the patient is a type 2 diabetic, who as a group usually tests before meals, the message 425 may be dispensed with entirely. In an alternative embodiment, however, step 425 may include a message asking the user or patient to test or measure their blood glucose level more often, in the future, during a prescribed or determined time period as compared to any comparable prior time periods.

Figure 14B:
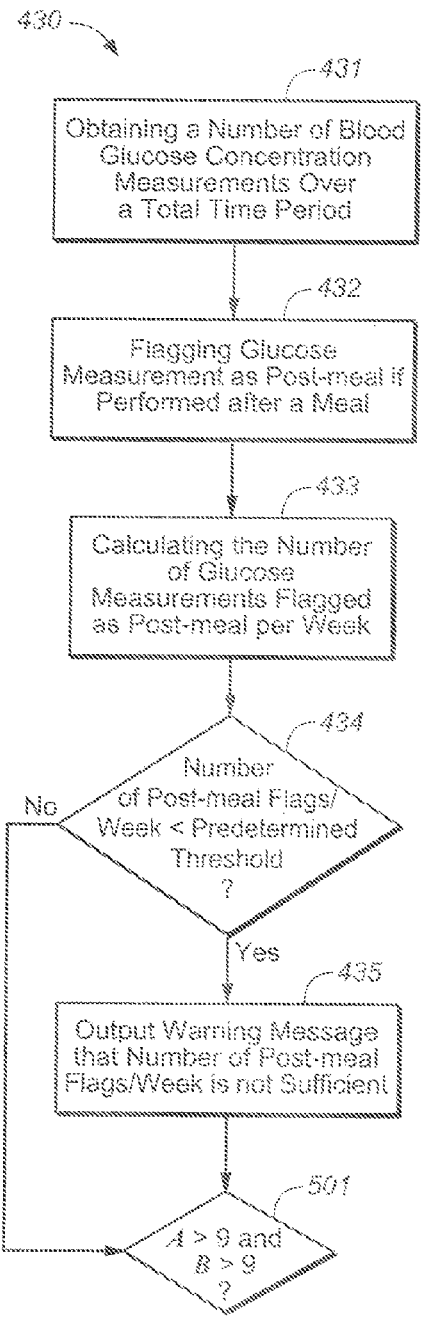
FIG. 14B illustrates a flow chart for analyzing a plurality of glucose concentration measurements for a pattern that may indicate whether the adequacy of post-meal testing is sufficient.

FIG. 14B shows a flow chart for the adequacy of post-meal testing sub-routine 430, which may include obtaining a number of blood glucose measurements over a total time period, as shown in step 431. Next, the blood glucose concentration measurement may be flagged as post-meal if the blood glucose concentration measurement was performed after a meal, as shown in step 432. A number of blood glucose concentration measurements per week that are flagged as post-meal can be determined, as shown in step 433. In step 434, the number of blood glucose concentration measurements flagged as post-meal per week is compared to a pre-determined threshold. A warning message may be displayed if the number of blood glucose concentration measurements per week that are flagged as post-meal is less than a pre-determined threshold, as shown in step 435. However, it should be noted that the appropriate threshold is one that can be set by the physician or automatically or semi-automatically via a suitable algorithm by taking into account the average number of tests per day or per week, the pattern of testing being used, and the pattern of testing recommended by the physician. In one embodiment, the pre-determined threshold may range from about 3 post-meal flags per week to about 7 post-meal flags per week. If the number of blood glucose concentration measurements per week that are flagged as post-meal is not less than a pre-determined threshold, then the sub-routine 430 may move to the step 501, where A indicates pre-meal testing frequency and B indicates post-meal testing frequency. After displaying the message in step 435, the sub-routine 430 may move to the step 501.

Figure 14C:
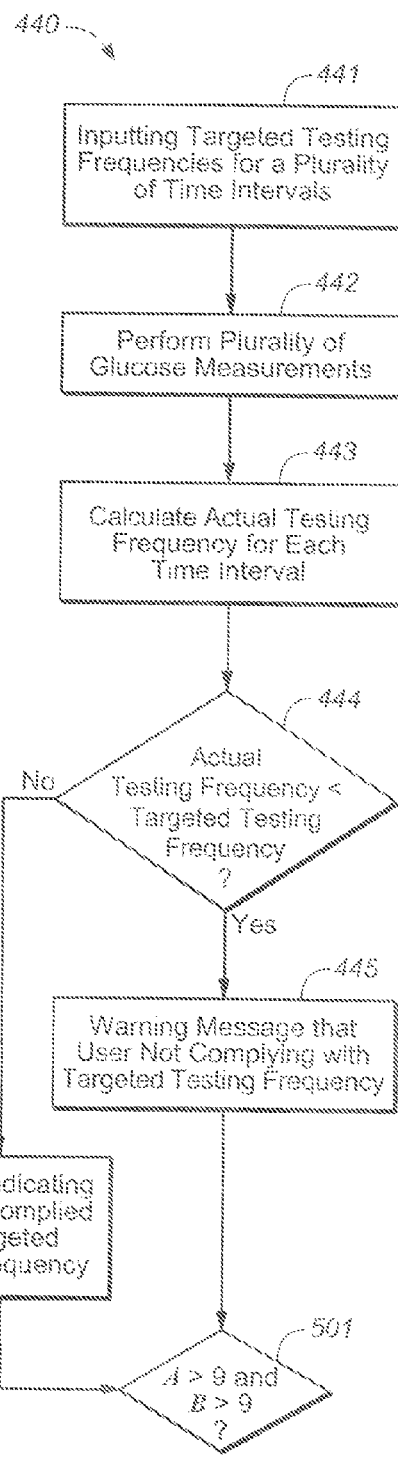
FIG. 14C illustrates a flow chart for analyzing a plurality of glucose concentration measurements for determining whether a user is complying with a targeted testing frequency.

In an alternative embodiment, the adequacy of blood glucose testing sub-routine 440 may be performed after the adequacy of post-meal testing sub-routine 430. FIG. 14C shows a flow chart for the adequacy of blood glucose testing sub-routine 440 that helps a physician determine a user's compliance in performing a sufficient number of blood glucose measurements. The adequacy of blood glucose testing sub-routine 440 may include inputting a plurality of targeted testing frequencies for a plurality of time intervals, as shown in step 441. The time intervals may include before breakfast, after breakfast, before lunch, after lunch, before dinner, after dinner, bedtime, and overnight. In one embodiment, a physician may input a targeted testing frequency for all of the time intervals to provide targeted goals for the user. Next, a number of blood glucose measurements may be performed at various time intervals, as shown in step 442. An actual testing frequency for each time interval may be calculated, as shown in step 443. In step 444, the actual testing frequency is compared to the targeted testing frequency. A warning message may be displayed if the actual testing frequency is less than the targeted testing frequency, as shown in step 445. If the actual testing frequency is not less than the targeted testing frequency, then a message indicating the user had complied with the targeted testing frequencies, as shown in step 446. After displaying the message in either step 445 or step 446, the sub-routine 440 may move to the step 501.

In another alternative embodiment, the testing/dosing pattern 400 may include sub-routines for recognizing patterns indicative of a pre-meal or post meal blood glucose measurements. A message may be displayed alerting a user that the most recently performed blood glucose measurement is pre-meal or post-meal based on past blood glucose measurements. The user may then be provided the option of flagging the blood glucose measurement with the appropriate flag.

Figure 15:
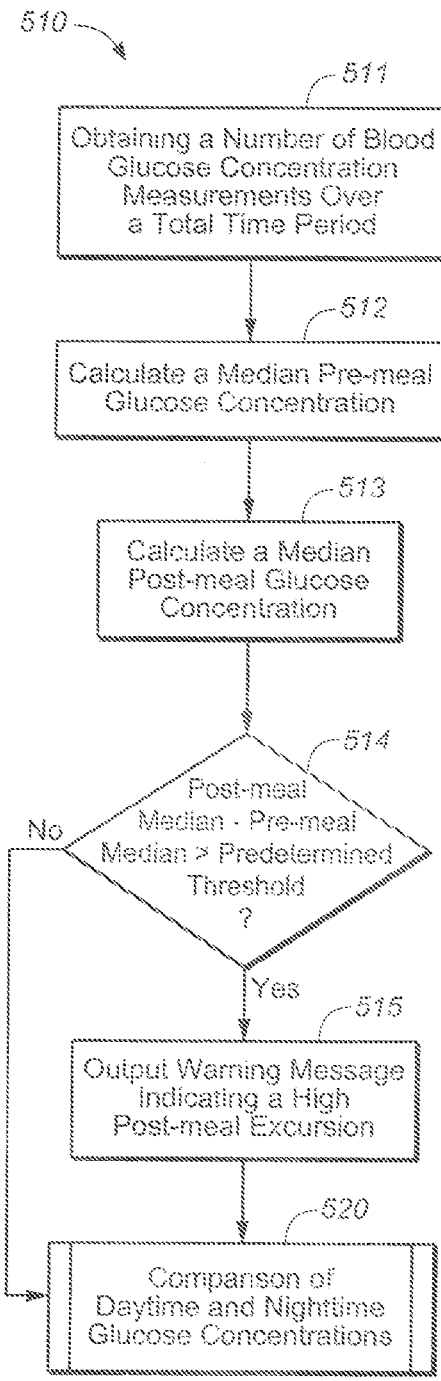
FIG. 15 illustrates a flow chart for analyzing a plurality of glucose concentration measurements for comparing pre-meal and post-meal glucose concentrations.

FIG. 15 shows a flow chart for the comparison of pre-meal and post-meal blood glucose concentrations sub-routine 510, which may be used to determine whether there is a significant increase in blood glucose concentration after a user has ingested a meal. The comparison of pre-meal and post-meal blood glucose concentrations sub-routine 510 may include obtaining a number for blood glucose concentration measurements, as shown in step 511. Next, a median pre-meal blood glucose concentration and a median post-meal blood glucose concentration may be calculated, as shown in steps 512 and 513, respectively. Pre-meal and post-meal blood glucose concentrations may be defined as blood glucose concentration measurements that are flagged as pre-meal and post-meal, respectively. In step 514, the median pre-meal glucose concentration is subtracted from the median post-meal glucose concentration that results in a difference value. The difference value can be a clinically significant, statistically or both clinically and statistically significant value depending on the types of meal involved. A warning message indicating a high post-meal excursion if the difference value is greater than a pre-determined threshold, as shown in step 515. If the difference value is not greater than a pre-determined threshold, then the sub-routine 510 may move to the comparison of daytime and nighttime glucose concentrations sub-routine 520. After displaying the message in step 512, the sub-routine 510 may move to the comparison of daytime and nighttime glucose concentrations sub-routine 520. In one embodiment, the pre-determined threshold may be about 50 mg/dL. An embodiment may include a pre-condition where a warning message is not displayed unless there are greater than about nine measurements that are flagged as pre-meal and greater than about nine measurements that are flagged as post-meal.

Figure 16:
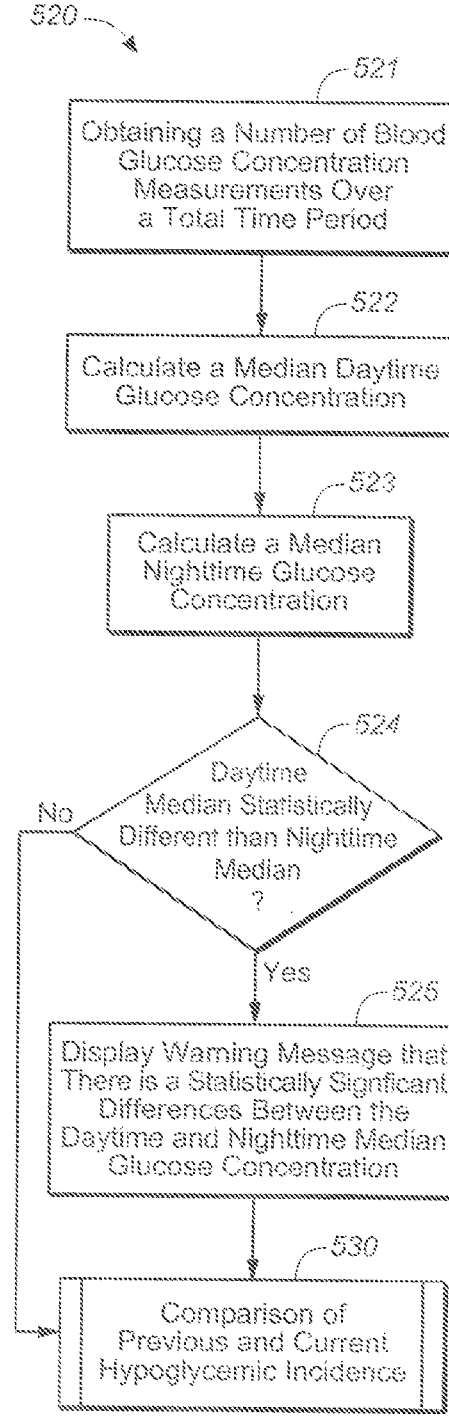
FIG. 16 illustrates a flow chart for analyzing a plurality of glucose concentration measurements for comparing daytime and nighttime glucose concentrations.

FIG. 16 shows a flow chart for the comparison of daytime and nighttime glucose concentrations sub-routine 520, which may be used to determine whether there is a significant difference in daytime and nighttime glucose concentrations. The comparison of daytime and nighttime glucose concentrations sub-routine 520 may include obtaining a number for blood glucose measurements over a total time period, as shown in step 521. Next, a median daytime glucose concentration and nighttime glucose concentration may be calculated, as shown in steps 522 and 523, respectively. Daytime may be a time interval ranging from about 6:00 A.M. to about 4:59 P.M. Nighttime may be a time interval ranging from about 5:00 P.M. to about 5:59 A.M. However, a daytime or nighttime period can be of any predetermined time periods, as selected by the physician or clinician. Next, a statistical test may be used to determine whether the daytime median is statistically significantly different from the nighttime median, as shown in step 524. If there are statistically significant differences, a warning message may be displayed indicating a difference between the daytime median and the nighttime median, as shown in step 525. If there is not a statistically significant difference, the sub-routine 520 may move to the comparison of previous and current hypoglycemic incidence sub-routine 530. After displaying the message in step 525, the sub-routine 520 may move to the comparison of previous and current hypoglycemic incidence sub-routine 530.

In one embodiment, the statistical test is a non-parametric statistical test. The non-parametric statistical test may be a Wilcoxon test or a Rank Sum test. The non-parametric test may include combining a plurality of glucose concentration measurements performed at the daytime time interval and at the nighttime time interval to form an aggregate of glucose concentration measurements. Next, the aggregate of glucose concentration measurements may be ranked in an ordinal order and a standardized rank sum $W_{std}$ may be calculated using an Equation 15.

$$W_{std} = \frac{W_d - \left[\frac{M_d * (N_d + N_n + 1)}{2}\right]}{\sqrt{\frac{N_d * N_n * (N_d + N_n + 1)}{12}}} \quad \text{Eq. 15}$$

In Equation 15, the terms $W_{std}$ represents the standardized rank sum, $W_d$ represents a rank sum of the plurality of glucose concentration measurements performed at the daytime time interval, $N_d$ is the number of glucose concentration measurements for the daytime interval, and $N_n$ is the number of glucose concentration measurements for the nighttime interval. A warning message may be displayed indicating a statistically significant difference between the daytime median and the nighttime median if the standardized rank sum is greater than about 2. In one embodiment, the warning message may be displayed if the plurality of glucose concentration measurements performed at the daytime includes more than about 9 measurements. In another embodiment, the warning message may be displayed if the plurality of glucose concentration measurements performed at the nighttime includes more than about 9 measurements.

In another embodiment, the non-parametric test may be performed using a different equation if two or more glucose concentrations have a tie (i.e., have the same value). When two or more glucose concentrations have a tie, a standardized rank sum $W_{std}$ may be calculated using an Equation 16.

$$W_{std} = \frac{W_d - \left[\frac{N_d * (N_d + N_n + 1)}{2}\right]}{\left[\frac{N_d * N_n * (N_d + N_n + 1)}{12}\right] - \left\{\frac{N_d * N_n}{12 * (N_d + N_n) * (N_d + N_a - 1)} * \sum_{j=1}^{g}(h_j - 1) * h_i * (h_j + 1)\right\}} \quad \text{Eq. 16}$$

In Equation 16, the term $h_j$ represents a number of glucose concentration values within a tie, j represents an index value associated with each group of glucose concentrations having a tie, and g is a total number of ties. For example, if the blood glucose concentration values are 93, 93, 100, 100, 100, 104, 104, 104, 104 mg/dL, then $h_1=2$, $h_2=3$, $h_3=4$, and g=3. A warning message may be displayed indicating a statistically significant difference between the daytime median and the nighttime median if the standardized rank sum is greater than about 2.

Figure 17A:
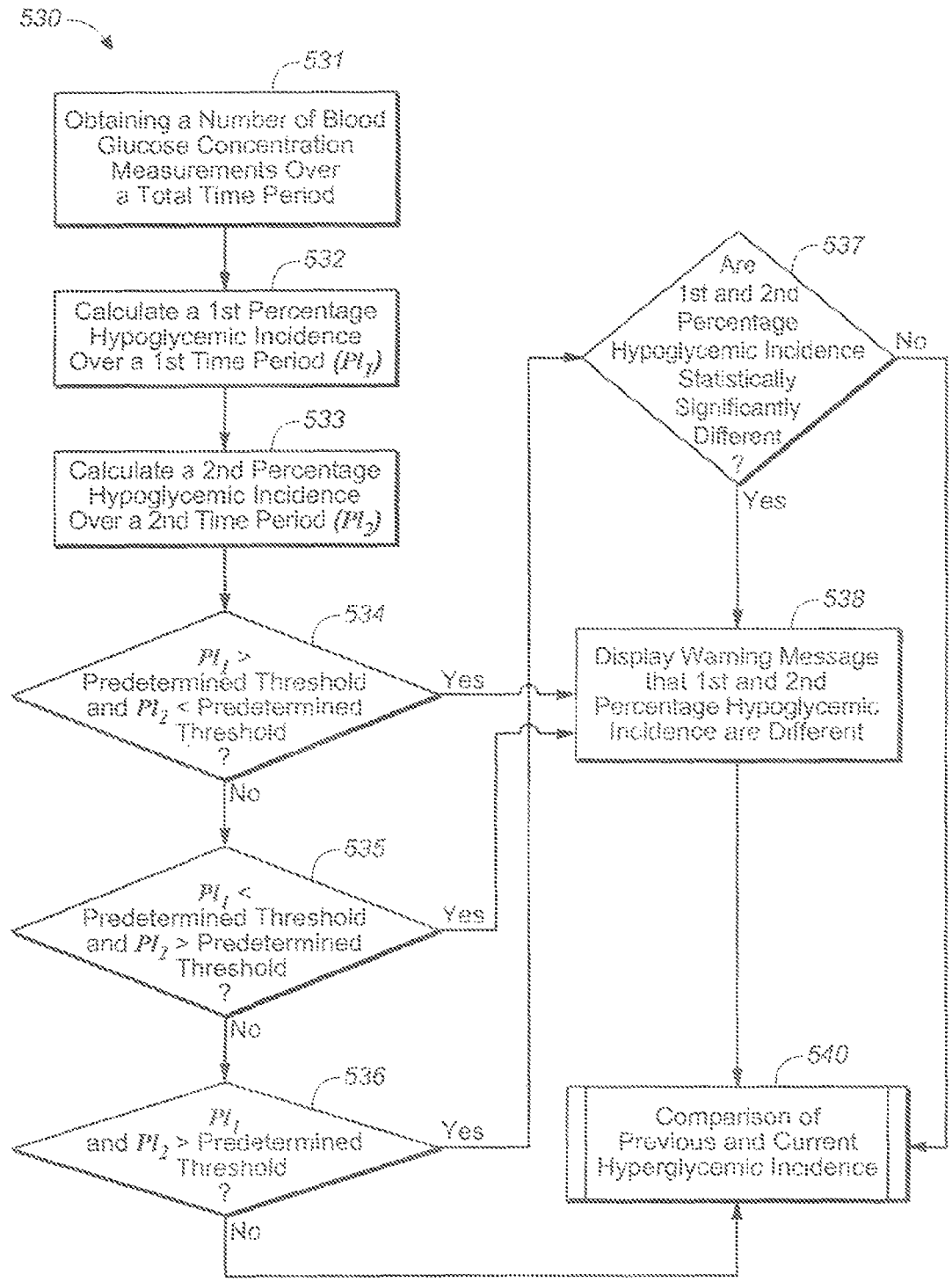
FIG. 17A illustrates a flow chart for analyzing a plurality of glucose concentration measurements for comparing previous and current hypoglycemic incidence.

FIG. 17A shows the comparison of previous and current hypoglycemic incidence sub-routine 530, which may indicate a statistical change from a current reporting period and a previous reporting period. A reporting period may be defined as the period between two successive device downloads for a given user. Note that the device does not have to be the same from download to download.

The comparison of previous and current hypoglycemic incidence sub-routine 530 may include obtaining a number of blood glucose measurements over a total time period, as shown in step 531. Next, a first percentage of hypoglycemic incidence $Pl_1$ may be calculated over a first time period, as shown in step 532. A second percentage of hypoglycemic incidence $Pl_2$ may be calculated over a second time period, as shown in step 533. The first time period may be a current time period and the second time period may be a previous time period.

In step 534, a calculation may be performed for determining if two conditions are achieved which are whether the first percentage of hypoglycemic incidence $Pl_1$ is greater than a pre-determined threshold and whether the second percentage of hypoglycemic incidence $Pl_2$ less than a pre-determined threshold. If both of the above two conditions in step 534 are met, then the sub-routine 530 may show a warning message indicating a difference between the first percentage of hypoglycemic incidence $Pl_1$ and the second percentage of hypoglycemic incidence $Pl_2$, as shown in step 538. If at least one of the above two conditions are not met in step 534, then the sub-routine may move to step 535.

In the step 535, a calculation may be performed for determining if two conditions are achieved which are whether the first percentage of hypoglycemic incidence $Pl_1$ is less than a pre-determined threshold and whether the second percentage of hypoglycemic incidence $Pl_2$ is greater than a pre-determined threshold. If both of the above two conditions in step 535 are met, then the sub-routine 530 may show a warning message indicating a difference between the first percentage of hypoglycemic incidence $Pl_1$ and the second percentage of hypoglycemic incidence $Pl_2$, as shown in step 538. If at least one of the above two conditions are not met in step 535, then the sub-routine may move to step 536.

In the step 536, a calculation may be performed for determining whether the first percentage of hypoglycemic incidence $Pl_1$ and second percentage of hypoglycemic incidence $Pl_2$ are greater than a pre-determined threshold. If the above condition in step 536 is met, then the sub-routine 530 may perform a calculation for determining whether the first percentage of hypoglycemic incidence $Pl_1$ is statistically significantly different than the second percentage of hypoglycemic incidence $Pl_2$, as shown in step 537. If the above condition in step 536 is not met, then the sub-routine 530 may move to the comparison of previous and current hyperglycemic incidence sub-routine 540.

A calculation may be performed for determining whether the first percentage of hypoglycemic incidence $Pl_1$ is statistically significantly different than the second percentage of hypoglycemic incidence $Pl_2$, as shown in step 537. If a statistically significant difference is found between the first and second percentage of hypoglycemic incidence, a warning message may be displayed indicating the difference, as shown in step 538. If a statistically significant difference is not found between the first and second percentage of hypoglycemic incidence, the sub-routine 530 may move to the comparison of previous and current hyperglycemic incidence sub-routine 540. After displaying the message in the step 538, the sub-routine 530 may move to the comparison of previous and current hyperglycemic incidence sub-routine 540. In an embodiment of the comparison of previous and current hypoglycemic incidence sub-routine 530, the threshold may be about five percent or greater.

In one embodiment, a Z test may be used to determine whether the first percentage of hypoglycemic incidence is statistically significantly different than the second percentage of hypoglycemic incidence. The Z test may be performed using Equation 17.

$$Z = \frac{Pl_1 - Pl_2}{\sqrt{\left[\frac{Pl_1 * (1 - Pl_1)}{Nl_1}\right] + \left[\frac{Pl_2 * (1 - Pl_2)}{Nl_2}\right]}} \quad \text{Eq. 17}$$

In Equation 17, the terms $Pl_1$ is the first percentage of hypoglycemic incidence, $Pl_2$ is the second percentage of hypoglycemic incidence, $Nl_1$ is the number of substantially hypoglycemic blood glucose concentration measurements that occur during the first time period, and $Nl_2$ is the number of substantially hypoglycemic blood glucose concentration measurements that occur during the second time period. A warning message may be displayed indicating a statistically significant difference between the first and second percentage of hypoglycemic incidence if Z is greater than about 2. In one embodiment, the warning message may be displayed if the number of substantially hypoglycemic blood glucose concentration measurements that occur during the first or second time period is greater than about 27.

Figure 17B:
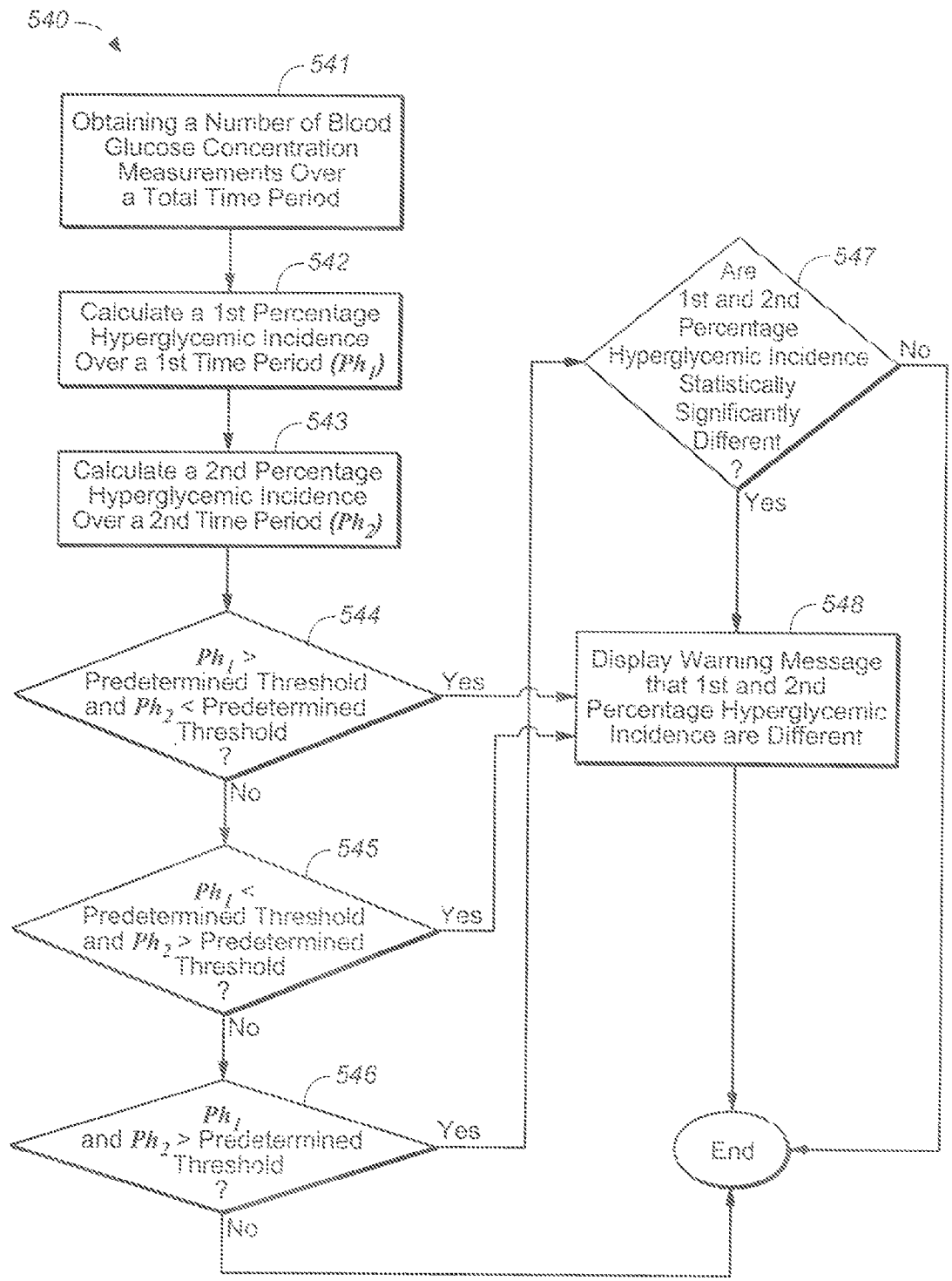
FIG. 17B illustrates a flow chart for analyzing a plurality of glucose concentration measurements for comparing previous and current hyperglycemic incidence.

FIG. 17B shows the comparison of previous and current hyperglycemic incidence sub-routine 540, which may indicate a statistical change from a current reporting period and a previous reporting period. A reporting period may be defined as the period between two successive device downloads for a given user. Note that the device does not have to be the same from download to download.

The comparison of previous and current hyperglycemic incidence sub-routine 540 may include obtaining a number of blood glucose measurements over a total time period, as shown in step 541. Next, a first percentage of hyperglycemic incidence $Ph_1$ may be calculated over a first time period, as shown in step 542. A second percentage of hyperglycemic incidence $Ph_2$ may be calculated over a second time period, as shown in step 543. The first time period may be a current time period and the second time period may be a previous time period.

In step 544, a calculation may be performed for determining if two conditions are achieved which are whether the first percentage of hyperglycemic incidence $Ph_1$ is greater than a pre-determined threshold and whether the second percentage of hyperglycemic incidence $Ph_2$ is less than a pre-determined threshold. If both of the above two conditions in step 544 are met, then the sub-routine 540 may show a warning message indicating a difference between the first percentage of hyperglycemic incidence $Ph_1$ and the second percentage of hyperglycemic incidence $Ph_2$, as shown in step 548. If at least one of the above two conditions are not met in step 544, then the sub-routine may move to step 545.

In the step 545, a calculation may be performed for determining if two conditions are achieved which are whether the first percentage of hyperglycemic incidence $Ph_1$ is less than a pre-determined threshold and whether the second percentage of hyperglycemic incidence $Ph_2$ greater than a pre-determined threshold. If both of the above two conditions in step 545 are met, then the sub-routine 540 may show a warning message indicating a difference between the first percentage of hyperglycemic incidence $Ph_1$ and the second percentage of hyperglycemic incidence $Ph_2$, as shown in step 548. If at least one of the above two conditions are not met in step 545, then the sub-routine may move to step 546.

In the step 546, a calculation may be performed for determining whether the first percentage of hyperglycemic incidence $Ph_1$ and second percentage of hyperglycemic incidence $Ph_2$ are greater than a pre-determined threshold. If the above condition in step 546 is met, then the sub-routine 540 may perform a calculation for determining whether the first percentage of hyperglycemic incidence $Ph_1$ is statistically significantly different than the second percentage of hyperglycemic incidence $Ph_2$, as shown in step 547. If the above condition in step 546 is not met, then the sub-routine 540 may move to the end.

A calculation may be performed for determining whether the first percentage of hyperglycemic incidence $Ph_1$ is statistically significantly different than the second percentage of hyperglycemic incidence $Ph_2$, as shown in step 547. If a statistically significant difference is found between the first and second percentage of hyperglycemic incidence, a warning message may be displayed indicating the difference, as shown in step 548. If a statistically significant difference is not found between the first and second percentage of hyperglycemic incidence, the sub-routine 540 may move to the end. After displaying the message in the step 548, the sub-routine 540 may move to the end. In an embodiment of the comparison of previous and current hyperglycemic incidence sub-routine 540, the threshold may be about fifty percent or greater.

In one embodiment, a Z test may be used to determine whether the first percentage of hyperglycemic incidence is statistically significantly different than the second percentage of hyperglycemic incidence. The Z test may be performed using Equation 18.

$$Z = \frac{Ph_1 - Ph_2}{\sqrt{\left[\frac{Ph_1 * (1 - Ph_1)}{Nh_1}\right] + \left[\frac{Ph_2 * (1 - Ph_2)}{Nh_2}\right]}} \quad \text{Eq. 18}$$

In Equation 18, the terms $Ph_1$ is the first percentage of hyperglycemic incidence, $Ph_2$ is the second percentage of hyperglycemic incidence, $Nh_1$ is the number of substantially hyperglycemic blood glucose concentration measurements that occur during the first time period, and $Nh_2$ is the number of substantially hyperglycemic blood glucose concentration measurements that occur during the second time period. A warning message may be displayed indicating a statistically significant difference between the first and second percentage of hyperglycemic incidence if Z is greater than about 2. In one embodiment, the warning message may be displayed if the number of substantially hyperglycemic blood glucose concentration measurements that occur during the first or second time period is greater than about 27.

It should be noted here that while the glucose concentration in a patient is preferably obtained via the patient's blood for various exemplary embodiments, other physiological fluids from the patient can be utilized to provide a determination of glucose level such as, for example, interstitial fluid. Accordingly, it is intended that the word "glucose" (whether used herein alone or in conjunction with the word "blood," as in "blood glucose" or "glucose") to define not only glucose concentration or value present in blood but also in other biological fluids such as, for example, glucose concentration in interstitial fluid.

Figure 18:
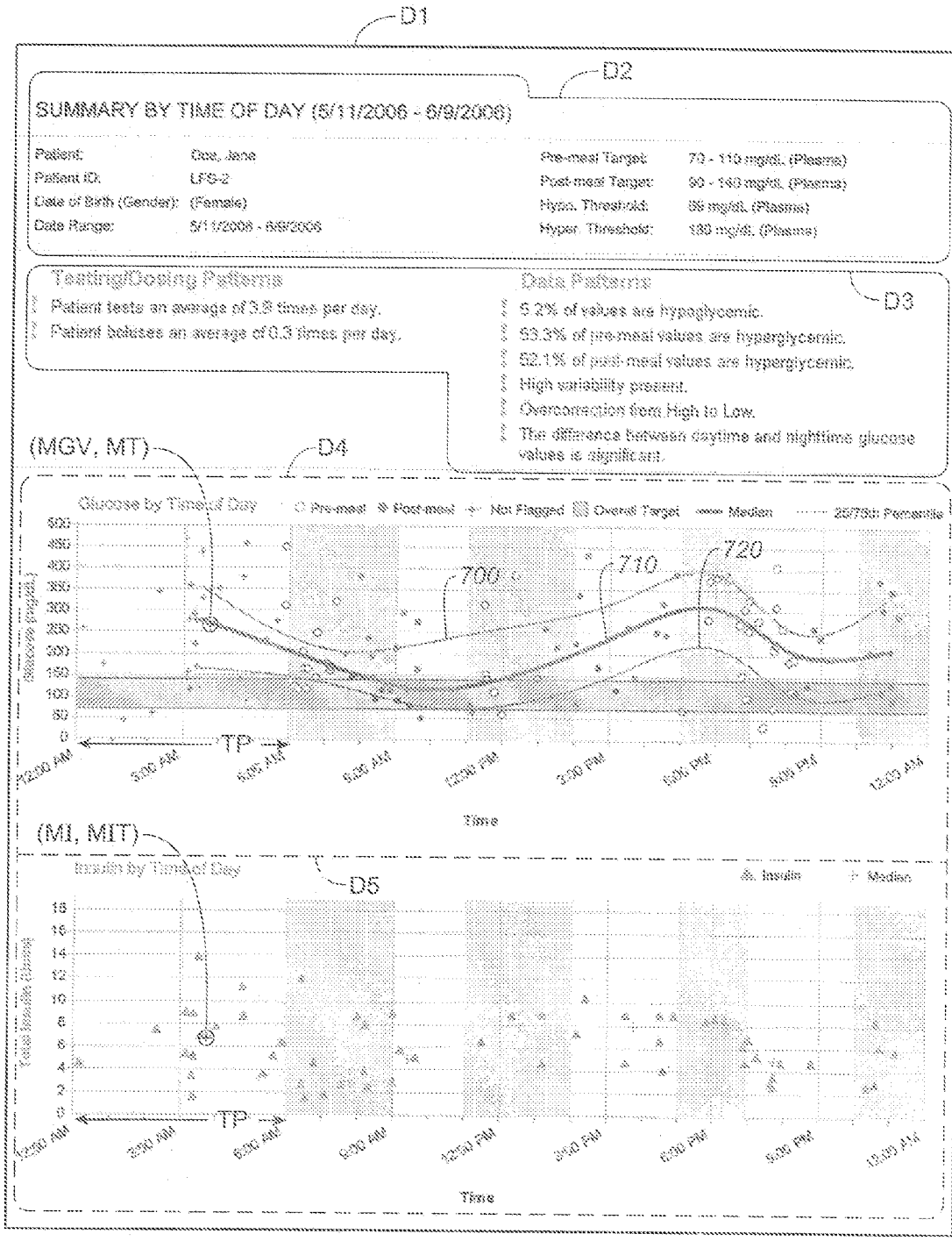
FIG. 18 illustrates a summary report by time of day generated using an embodiment of the diabetes management system.

By virtue of the disclosure and illustrations provided herein, applicants have provided a communication medium to assist in diabetes management. The communication medium, as shown in FIG. 18, includes a first display area D1 that has second, third, fourth, and fifth display areas D2, D3, D4, and D5, respectively, in the first display area. The second display area D2 has identification information of a patient, whereas the third display area D3 has a plurality of textual messages, and the fourth display area D4 includes a graphical chart indicative of a variability of the glucose concentration over a predetermined time period of the patient, and other suitable information in graphical or textual format. The fifth display area D5 has a graphical chart of units of insulin taken over time for the patient. In the exemplary embodiments, the first display area D1 includes a display selected from any one of a video display monitor, a light projector, a sheet of paper, a hologram, an audio representation of the patient's variability trends (e.g., an automated voice response to the patient stating "high-variability between the hours of 3 A.M. and 9 A.M.) or combinations thereof.

The third display area D3 includes display of information for at least one of but are not limited to (a) incidence of hypoglycemia (b) incidence of hyperglycemia (c) blood glucose variability, (d) overcorrection, (e) differential between night time glucose concentration versus daytime glucose concentration, and (f) comparative analysis of glycemic state of the patient for a time period or at different time periods. In particular, the incidence of hypoglycemia includes (i) incidence of hypoglycemia by time period, (ii) incidence of hypoglycemia by day of the week, (iii) incidence of pre-meal hypoglycemia, and (iv) incidence of post-meal hypoglycemia. In other words, the third display area has a plurality of textual messages indicative of diabetes status of the patient including hypoglycemia, hyperglycemia, or excessive blood glucose variability.

Further, the incidence of hypoglycemia includes a textual indication of hypoglycemic incidence that includes a calculated percentage of hypoglycemic events within a predetermined time period, which is provided whenever the calculated percentage is greater than about 5% or a textual indication that all glucose readings are hypoglycemic is provided whenever the calculated percentage is 100%, otherwise no textual indication of hypoglycemic incidence is provided. A textual display of an indication of higher hypoglycemia in a specific time period is provided whenever a statistical correlation is determined between a time slot and a hypoglycemic event and there is an indication of hypoglycemic incidence. A textual display of an indication of higher hypoglycemia in a specific day of the week is provided whenever a statistical correlation is determined between the day of the week and a hypoglycemic event and there is a textual indication of hypoglycemic incidence. A textual display of pre-meal hypoglycemic events is provided whenever there are more than about 5% of pre-meal glucose readings marked as pre-meal glucose readings within a predetermined time period. Conversely, a textual display of post-meal hypoglycemic events is provided whenever there are more than about 5% of glucose readings marked as post-meal glucose readings within a predetermined time period.

The fourth display area D4 includes a graphical pattern of blood glucose variability about a median blood glucose value by at least one of time of day, of day in a week, of both time of day and day of week, or at different predetermined intervals. Although a graphical blood glucose variability pattern is shown in FIG. 18 in relation to a specific day as spanning from 24 hours starting at about 12 A.M. to about 12 A.M., other relations can be also be viewed, as described earlier, in relation to day of a week, both time and day of week, specific date in a week or month, or over predetermined intervals, such as between physician's office visits or between different prescribed therapeutic regimens.

The communication medium also has the ability to provide information regarding incidence of hyperglycemia that includes but are not limited to (i) incidence of hyperglycemia by time period, (ii) incidence of hyperglycemia by day of the week, (iii) incidence of pre-meal hyperglycemia, and (iv) incidence of post-meal hyperglycemia. In particular, the incidence of hyperglycemia includes a textual indication of hyperglycemic incidence that includes a calculated percentage of hyperglycemic events within a predetermined time period is provided whenever the calculated percentage is greater than about 15% or a textual indication that all glucose readings are hyperglycemic is provided whenever the calculated percentage is 100%, otherwise no textual indication of hyperglycemic incidence is provided. Whenever a statistical correlation is determined between a time slot and a hyperglycemic event and there is a textual indication of hyperglycemic incidence, a textual display of an indication of higher hyperglycemia in a specific time period is provided. A textual display of an indication of higher hyperglycemia in a specific day of the week is provided whenever a statistical correlation is determined between the day of the week and a hyperglycemic event and there is a textual indication of hyperglycemic incidence. Whenever there is more than about 5% of glucose readings marked as post-meal glucose readings within a predetermined time period, a textual display of pre-meal hyperglycemic events is provided. And whenever there is more than about 5% of glucose readings marked as pre-meal glucose readings within a predetermined time period, a textual display of post-meal hyperglycemic events is also provided. Although 5% has been selected as a threshold, other values can be utilized depending on the therapeutic regimen prescribed by a physician, such as, for example, 10% or 15%.

The communication medium also has the ability to provide information relating to glucose variability, including, but not limited to (i) glucose variability range, (ii) possible rebound from hypoglycemia to hyperglycemia, (iii) incidence of possible overcorrection from hyperglycemia to hypoglycemia, or (iv) blood glucose variability associated with a specified indicator such as, for example, a specific time period during a day, a plurality of time periods in a day, a specified day in a week, a plurality of specified days in a week, pre-meal tests in a specific time period during a day, frequency of glucose measurements (i.e., testing) for pre-meal test for a specified day of the week, frequency of glucose measurements (i.e., testing) for pre-meal test for specified days of the week, glucose testing frequency having post-meal tests in a specific time period dining a day, frequency of glucose measurements (i.e., testing) for post-meal test for a specified day of the week, or frequency of glucose measurements (i.e., testing) for post-meal test for specified days of the week. A textual display indicative of high blood glucose variability is provided whenever a calculated blood glucose variability of a patient within a predetermined time period is about or greater than about a selected value, such as, for example, any value from about 30 mg/dL to about 90 milligrams per deciliter of glucose. A textual display indicative of a possibility of hypoglycemia to hyperglycemia rebound is provided whenever there is a change from a hyperglycemic event to a hypoglycemic event within a predetermined time period of less than about 4 hours. Whenever there is a change from a hypoglycemic event to a hyperglycemic event within a predetermined time period of less than about 4 hours, a textual display indicative of hyperglycemia to hypoglycemia rebound is provided.

Additionally, the communication medium can also provide information relating to differentials between pre and post meal data. Specifically, a textual indication of a calculated difference between pre-meal and post-meal medians within a reporting period is provided when the calculated difference is greater than about a selected value, such as, for example, any value from about 30 mg/dL to about 90 mg/dL, and preferably about 50 mg/dL.

Further, the communication medium can also provide information relating to hypo or hyper glycemic trends including a textual indication of one of an upward hypoglycemic trend or downward hypoglycemic trend based on a number of hypoglycemic measurement for two or more time periods, and a total number of glucose measurements for all of the time periods, as described earlier. Conversely, a textual indication of one of an upward hyperglycemic trend or downward hyperglycemic trend based on a number of hypoglycemic measurement for two or more time periods, and a total number of glucose measurements for all of the time periods. As used herein, the term "textual" is intended to cover not only text type representations but also numerical values, symbols (moving or stationary), charts, holograms, graphs, or combinations thereof.

Applicants have also, by virtue of the description and illustrations provided herein, provided for a computer program to provide diabetes management information to a user, which may include a clinician or a diabetic patient. The computer program includes a user interface, business object module, and a diabetes management rules engine, illustrated here in FIG. 1 and described earlier. The diabetes rule management engine generates a plurality of textual pattern recognition messages based on a plurality of data inputs relating to blood glucose of a patient, including a graphical chart indicative of a blood glucose variability of the glucose concentration over a predetermined time period of the patient.

The plurality of textual messages may include information for at least one of but are not limited to (a) incidence of hypoglycemia (b) incidence of hyperglycemia (c) blood glucose variability, (d) overcorrection, (e) differential between night time glucose concentration versus daytime glucose concentration, and (f) comparative analysis of hypoglycemic or hyperglycemic trends. In particular, the incidence of hypoglycemia includes (i) incidence of hypoglycemia by time period, (ii) incidence of hypoglycemia by day of the week, (iii) incidence of pre-meal hypoglycemia, and (iv) incidence of post-meal hypoglycemia. Further, the incidence of hypoglycemia includes a textual indication of hypoglycemic incidence that includes a calculated percentage of hypoglycemic events within a predetermined time period is provided whenever the calculated percentage is greater than about 5% or a textual indication that all glucose readings are hypoglycemic is provided whenever the calculated percentage is 100%, otherwise no textual indication of hypoglycemic incidence is provided. A textual display of an indication of higher hypoglycemia in a specific time period is provided whenever a statistical correlation is determined between a time slot and a hypoglycemic event and there is an indication of hypoglycemic incidence. A textual display of an indication of higher hypoglycemia in a specific day of the week is provided whenever a statistical correlation is determined between the day of the week and a hypoglycemic event and there is such indication of hypoglycemic incidence. A textual display of pre-meal hypoglycemic events is provided whenever there are more than about 5% of glucose readings marked as pre-meal glucose readings within a predetermined time period. Conversely, a textual display of post-meal hypoglycemic events is provided whenever there are more than about 5% of glucose readings marked as post-meal glucose readings within a predetermined time period.

The computer program also has the ability to provide information regarding incidence of hyperglycemia that includes but are not limited to (i) incidence of hyperglycemia by time period, (ii) incidence of hyperglycemia by day of the week, (iii) incidence of pre-meal hyperglycemia, and (iv) incidence of post-meal hyperglycemia. In particular, the incidence of hyperglycemia includes a textual indication of hyperglycemic incidence that includes a calculated percentage of hyperglycemic events within a predetermined time period is provided whenever the calculated percentage is greater than about 15% or a textual indication that all glucose readings are hyperglycemic is provided whenever the calculated percentage is 100%, otherwise no textual indication of hyperglycemic incidence is provided. A textual display of an indication of higher hyperglycemia in a specific time period is provided whenever a statistical correlation is determined between a time slot and a hyperglycemic event and there is a textual indication of hyperglycemic incidence. Similarly, a textual display of an indication of higher hyperglycemia in a specific day of the week is provided whenever a statistical correlation is determined between the day of the week and a hyperglycemic event and there is indication of hyperglycemic incidence. Additionally, a textual display of pre-meal hyperglycemic events is provided whenever there are more than about 5% of glucose readings marked as pre-meal glucose readings within a predetermined time period. A textual display of post-meal hyperglycemic events is provided whenever there are more than about 5% of glucose readings marked as post-meal glucose readings within a predetermined time period.

The computer program also has the ability to provide information relating to glucose variability, including, but not limited to (i) glucose variability range, (ii) a possibility of hypoglycemia to hyperglycemia rebound, (iii) incidence of possible overcorrection from hyperglycemia to hypoglycemia, or (iv) blood glucose variability associated with a specified indicator such as, for example, a specific time period during a day, a plurality of time periods in a day, a specified day in a week, a plurality of specified days in a week, pre-meal tests in a specific time period during a day, frequency of glucose measurements (i.e., testing) for pre-meal test for a specified day of the week, frequency of glucose measurements (i.e., testing) for pre-meal test for specified days of the week, glucose testing frequency having post-meal tests in a specific time period during a day, frequency of glucose measurements (i.e., testing) for post-meal test for a specified day of the week, or frequency of glucose measurements (i.e., testing) for post-meal test for specified days of the week. A textual display indicative of high blood glucose variability is provided whenever a calculated blood glucose variability of a patient within a predetermined time period is about or greater than about 90 milligram per deciliter. Whenever there is a change from a hyperglycemic event to a hypoglycemic event within a predetermined time period less than about 4 hours a textual display indicative of a possibility of hypoglycemia to hyperglycemia rebound is provided. Similarly, a textual display indicative of hyperglycemia to hypoglycemia rebound is provided whenever there is a change from a hypoglycemic event to a hyperglycemic event within a predetermined time period less than about 4 hours.

Additionally, the computer program can also provide information relating to differential between pre and post meal data. Specifically, a textual indication of a calculated difference between pre-meal and post-meal medians within a reporting period is provided when the calculated difference is greater than about a predetermined value such as, for example, any value from about 30 mg/dL to about 90 mg/dL, and preferably about 50 mg/dL of glucose.

Further, the computer program can also provide information relating to hypo glycemic or hyper glycemic trends including a textual indication of one of an upward hypoglycemic trend or downward hypoglycemic trend based on a number of hypoglycemic measurement for two or more time periods, and a total number of glucose measurements for all of the time periods, as described earlier. Conversely, a textual indication of one of an upward hyperglycemic trend or downward hyperglycemic trend based on a number of hypoglycemic measurement for two or more time periods, and a total number of glucose measurements for all of the time periods. Set forth below in Table 1 are examples of various pattern recognition textual messages that can be provided to a clinician or user in managing diabetes:

TABLE 1

Exemplary Pattern Recognition Messages

| Message Nos. | Pattern Recognition Messages |
|---|---|
| 01 | Average number of glucose tests per week is ___. |
| 02 | Average number of glucose tests per week flagged as pre-meal is ___. |
| 03 | Average number of glucose tests per week flagged as post-meal is ___. |
| 04 | ___% of values are hypoglycemic. |
| 05 | Higher incidence of hypoglycemia present for: ___. |
| 06 | ___% of pre-meal values are hypoglycemic. |
| 07 | ___% of post-meal values are hypoglycemic. |
| 08 | All glucose readings are hyperglycemic. |
| 09 | ___% of values are hyperglycemic. |
| 10 | Higher incidence of hyperglycemia present for: ___. |
| 11 | Higher incidence of hyperglycemia present for: ___. |
| 12 | ___% of pre-meal values are hyperglycemic. |
| 13 | ___% of post-meal values are hyperglycemic. |
| 14 | High variability present. |
| 15 | Rebound from Low to High. |
| 16 | Overcorrection from High to Low. |
| 17 | The difference between pre and post-meal medians is: ___ |
| 18 | The difference between daytime and nighttime glucose readings is significant. |

TABLE 1-continued

Exemplary Pattern Recognition Messages

| Message Nos. | Pattern Recognition Messages |
|---|---|
| 19 | Downward trend in the percentage of hypoglycemic values. |
| 20 | Downward trend in the percentage of hyperglycemic values. |
| 21 | .Note that no glucose tests were found in some time slots. |
| 22 | .Note that no glucose tests were found on certain days. |
| 23 | Nighttime readings are lower than daytime readings. |
| 24 | Daytime readings are lower than nighttime readings. |
| 25 | Upward trend in hypoglycemic events compared to the previous reporting period. |
| 26 | Downward trend in hypoglycemic events compared to the previous reporting period. |
| 27 | Upward trend in hyperglycemic events compared to the previous reporting period. |
| 28 | Downward trend in hyperglycemic events compared to the previous reporting period. |
| 29 | ___% of values are hypoglycemic. |
| 30 | Higher incidence of hypoglycemia present for: ___. Note that no glucose tests were found in some time slots. |
| 31 | Higher incidence of hypoglycemia present for: ___. Note that no glucose tests were found on certain days. |
| 32 | ___% of pre-meal values are hypoglycemic. |
| 33 | ___% of post-meal values are hypoglycemic. |
| 34 | ___% of values are hyperglycemic. |
| 35 | Higher incidence of hyperglycemia present for: ___. Note that no glucose tests were found in some time slots. |
| 36 | Higher incidence of hyperglycemia present for: ___. Note that no glucose tests were found on certain days. |
| 37 | ___% of pre-meal values are hyperglycemic. |
| 38 | ___% of post-meal values are hyperglycemic. |

The computer program via the diabetes management rules engine also correlates (a) a median of glucose concentration values during a temporal period and (b) a median of test times during the temporal period to define a data point on a graph having glucose values and test times. Further, the computer program via the diabetes management rule engine correlates (i) a median of insulin doses over a temporal period and (ii) a median of dosage time during the temporal period to define a data point on a graph having insulin doses and dosage times. As used herein, the temporal period includes, but is not limited to at least one of a specific time period during a day, a plurality of time periods in a day, a specified day in a week, or a plurality of specified days in a week. In particular, the temporal period may also include at least one of testing incidence or glucose testing frequency having pre-meal tests in a specific time period during a day, frequency of glucose measurements (i.e., testing) for pre-meal test for a specified day of the week, frequency of glucose measurements (i.e., testing) for pre-meal test for specified days of the week, testing incidence having post-meal tests in a specific time period during a day, frequency of glucose measurements (i.e., testing) for post-meal test for a specified day of the week, or frequency of glucose measurements (i.e., testing) for post-meal test for specified days of the week.

It is believed that one advantage of the various embodiments is the ability of the process (which includes processes, machine, system or method) to transform patient's data (e.g., blood glucose level, insulin injection or type of insulin, carbohydrates intakes etc.) so as to provide useful, concrete and tangible results such as, for example, patterns that are statistically or clinically significant in managing diabetes. For example, the system transform blood glucose data of a patient into textual patterns using statistical analysis to provide simple and direct explanation of various patterns rather than complicated charts and graphs of the same. Referring to FIG. 18, it can be seen that various "data patterns" such as, for example, percentage of data falling within hypoglycemic or hyperglycemic state, blood glucose variability, overcorrection, and differential between day and night blood glucose values are provided in clear and concise information for a busy clinician or user without the necessity of complicated graphs or tables. Other data can be presented in a graphical format to provide trends to a clinician such as, for example, pre-meal test time, post-meal test time, overall target and median glucose values. A pre-meal test time may be a time of a glucose measurement performed before eating a meal and a post-meal test time may be a time of a glucose measurement performed after eating a meal. And although blood glucose variability information can be provided in as simple text, shown here in display area D3, it is sometimes more informative to utilize a graphical format to convey trends in blood glucose variability, shown here in display area D4. As such, a graphical chart over time is provided that shows the blood glucose variability of the $1^{st}$ and $4^{th}$ interquartile ranges about a median glucose curve over time. Correlation between median blood glucose values (area D4) and median insulin injections (area D5) over the same time period (e.g., "TP", time of day, day of week, pre or post meal over a set time period) can be provided to a clinician interested in seeing a generalized effect of insulin or types of insulin on blood glucose value.

Figure 19A:
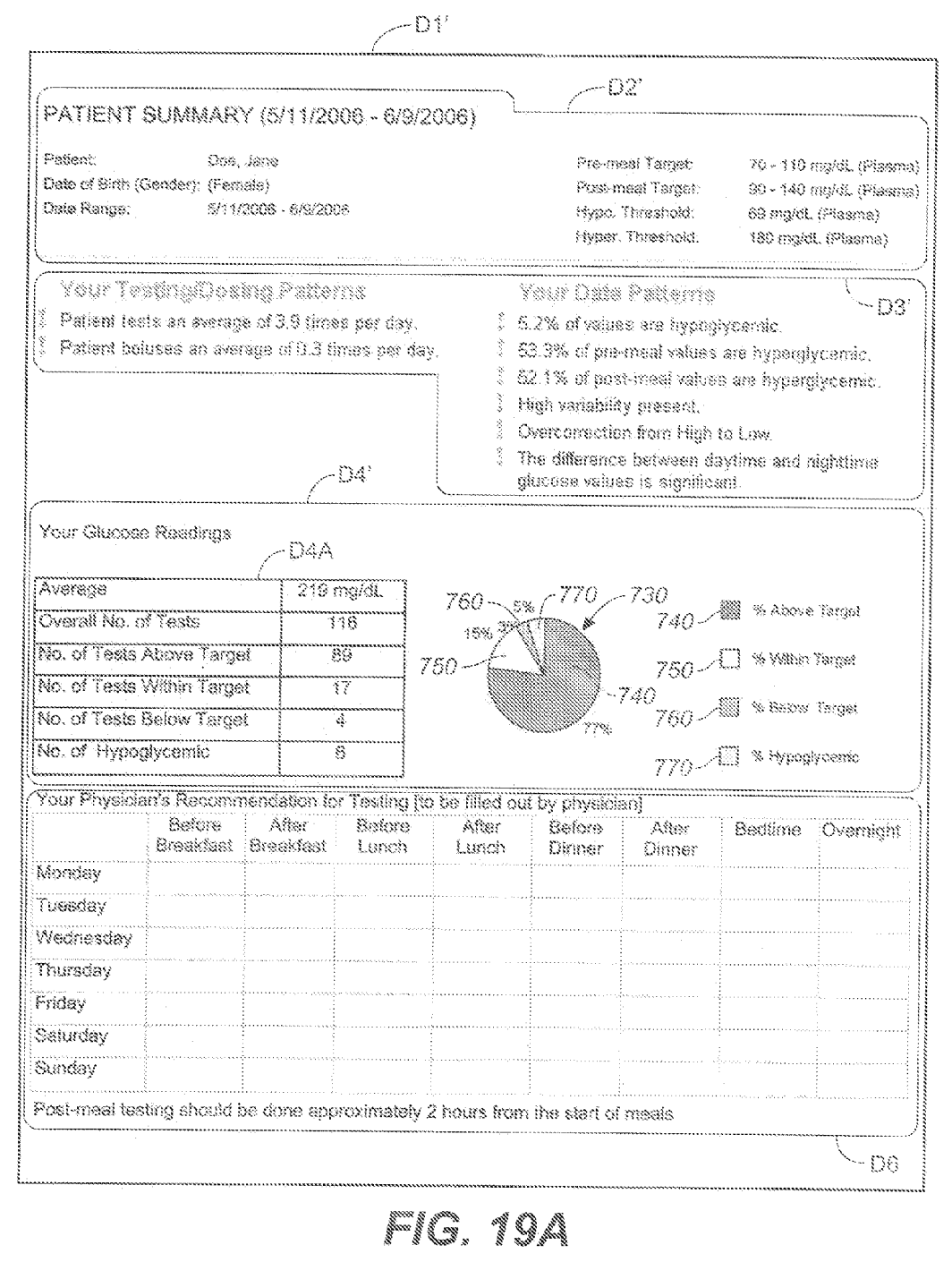

Referring to FIGS. 19A and 19B, the exemplary system also provides an alternative display format D1' for use by the patient after the visit with the physician or clinician. In particular, as shown in FIG. 19A, the display area D2' and D3' provide the same patient information as display area D1 of FIG. 18. Display area D4', however, provides for information that are believed to be more readily understood by a diabetic patient. For example, display area D4' shows the average blood glucose with the overall number of glucose measurements. The system further categorizes in table D4A the data into the number of tests above a target (which is set by the physician), below target and hypoglycemic. The system further provides a graphical chart 730 to demonstrate to the patient the data in table D4A in percentages. In the preferred embodiments, the graphical chart 730 is a pie chart showing the percentage (of a total number of tests in a predetermined time period) above target 740; percentage within target 750; percentage below target; and percentage hypoglycemic. A physician or clinician recommendation for testing is provided in area D6. Other information such as goals or targets is provided in display area D7.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially. Therefore, to the extent there are variations of the invention, which are within the spirit of the disclosure or equivalent to the inventions found in the claims, it is the intent that this patent will cover those variations as well.

What is claimed is:

1. A method of monitoring glycemia in a patient with a glucose meter that includes at least a power source, microprocessor, memory and display, the method comprising:

measuring, with a microprocessor of the meter, a plurality glucose concentrations of a patient with the glucose meter to provide a plurality of glucose measurements;

storing in the memory of the meter, the plurality of glucose measurements of the patient;

using the microprocessor, generating, from the memory, statistically significant patterns from the patient's glucose measurements, the patterns indicative of hypoglycemia, hyperglycemia, or excessive glucose variability by time of day, by day in a week, both by time of day and day of week, or at different time intervals which are selected from a group consisting of a time interval between visits to a physician, a time interval between visits to a clinician, a time interval between different prescribed therapies, and combinations thereof, the generating comprising:

determining a hypoglycemic pattern by:

obtaining a number of glucose measurements over a total time period;

dividing the total time period into a plurality of time intervals;

determining a percentage of hypoglycemic incidence for each of the time intervals which recurs daily and is equal to about one eighth of a day;

determining whether the percentage of hypoglycemic incidence for at least one of the time intervals is statistically significantly different;

displaying a message upon one of the patterns being indicative of a pattern of glycemia outside at least a predetermined range for such pattern with the display;

using the microprocessor, utilizing a chi-squared test to determine if any of the time intervals is statistically significantly different wherein the chi-squared test uses a confidence level ranging from about 95% to about 99%, the number of glucose measurements is greater than about 27, the chi-squared test is of the form:

$$\chi^2 = \sum_{i=1}^{n} \frac{(L_i - L_{i,pre})^2}{L_{i,pre}} + \sum_{i=1}^{n} \frac{(L'_i - L'_{i,pre})^2}{L'_{i,pre}}$$

where $\chi^2$=chi-squared, i represents a particular time interval, n is a total number of time intervals, $L_i$ is a number of substantially hypoglycemic glucose concentration measurements that occur during time interval i, $L_{i,pre}$ is a predicted number of substantially hypoglycemic glucose concentration measurements that will occur during time interval i, and $L'_{i,pre}$ is a predicted number of non-hypoglycemic glucose concentration measurements that will occur during interval time i, $L_{i,pre}$ using an estimation equation, the estimation equation comprising:

$$L_{i,pre} = \frac{\sum_{i=1}^{n} L_i}{\sum_{i=1}^{n} N_i} * N_i$$

where $N_i$ represents the total number of glucose concentration measurements performed during timer interval i;

comparing a calculated $\chi^2$ to a $\chi^2$ value in a table based on a number of degrees of freedom for each of said time intervals i, wherein the table includes a plurality of conditions that are related to at least two outcomes, one of which is a hypoglycemic outcome and the other of a non-hypoglycemic outcome; and determining that at least one of the time intervals are statistically significantly different if the calculated $\chi^2$ is greater than the $\chi^2$ value on the table.

2. The method of claim 1, further comprising:
calculating $Z_i$ using a Z test, the Z test comprising:

$$Z_i = \frac{(L_i - L_{i,pre})}{SE_i}$$

where $Z_i$ represents a Z value at a particular time interval i and $SE_i$ represents a standard error for a particular time interval i, the standard error $SE_i$ comprising:

$$SE_i = \sqrt{\frac{1}{N_i} * L_{i,pre} * (N_i - L_{i,pre})}$$

comparing a calculated $Z_i$ to a Z value in the table; and
identifying that one of the time intervals are statistically significantly different if the calculated $Z_i$ is greater than the Z value of about two.

3. The method of claim 1, wherein the generating comprises determining hyperglycemic patterns by:

obtaining a number of glucose measurements over a total time period;

dividing the total time period into a plurality of time intervals;

determining percentage of hyperglycemic incidence for each of the time intervals which recurs daily and is equal to about one eighth of a day;

determining whether the percentage of hyperglycemic incidence for at least one of the time intervals is statistically significantly different with a chi squared test $\chi^2$ with a confidence level ranging from about 95% to about 99% that comprises:

$$\chi^2 = \sum_{i=1}^{n} \frac{(H_i - H_{i,pre})^2}{H_{i,pre}} + \sum_{i=1}^{n} \frac{(H'_i - H'_{i,pre})^2}{H'_{i,pre}}$$

where $\chi^2$=chi-squared, i represents a particular time interval, n is a total number of time intervals, $H_i$ is a number of substantially hyperglycemic glucose concentration measurements that occur during time interval i, $H_{i,pre}$ is a predicted number of substantially hyperglycemic glucose concentration measurements that will occur during time interval i, where $H_{i,pre}$ comprises:

$$H_{i,pre} = \frac{\sum_{i=1}^{n} H_i}{\sum_{i=1}^{n} N_i} * N_i$$

where $N_i$ represents the total number of glucose concentration measurements performed during timer interval i, and $H'_{i,pre}$ is a predicted number of non-hyperglycemic glucose concentration measurements that will occur during time interval i;

comparing a calculated $\chi^2$ to a $\chi^2$ value in a table based on a number of degrees of freedom for each of said time intervals i; and determining that at least one of the time intervals are statistically significantly different if the calculated $\chi^2$ is greater than the $\chi^2$ value on the table;

identifying one of the time intervals as being statistically significantly different using a Z test comprising:

$$Z_i = \frac{(H_i - H_{i,pre})}{SE_i}$$

where $Z_i$ represents a Z value at a particular time interval i and $SE_i$ represents a standard error for a particular time interval i;

comparing a calculated $Z_i$ to a Z value in a table; and identifying that one of the time intervals are statistically significantly different if the calculated $Z_i$ is greater than the Z value of about two;

calculating $SE_i$, using a standard error equation, the standard error equation comprising:

$$SE_i = \sqrt{\frac{1}{N_i} * H_{i,pre} * (N_i - H_{i,pre})}; \text{ and}$$

displaying a message indicating a high incidence of hyperglycemia occurring on at least one of the time intervals based on the chi-squared and Z tests.

* * * * *